United States Patent
Weinberger et al.

(10) Patent No.: US 8,120,777 B2
(45) Date of Patent: Feb. 21, 2012

(54) TEMPERATURE-STABLE INTERFEROMETER

(75) Inventors: Scot R. Weinberger, Montara, CA (US); Bruce J. Richardson, Santa Cruz, CA (US); Darryl J. Bornhop, Nashville, TN (US)

(73) Assignees: Molecular Sensing, Inc., Montara, CA (US); Vanderbilt University, Nashville, TN (US)

( * ) Notice: Subject to any disclaimer, the term of this patent is extended or adjusted under 35 U.S.C. 154(b) by 307 days.

(21) Appl. No.: 12/331,354

(22) Filed: Dec. 9, 2008

(65) Prior Publication Data

US 2009/0185190 A1   Jul. 23, 2009

Related U.S. Application Data

(60) Provisional application No. 61/012,752, filed on Dec. 10, 2007.

(51) Int. Cl.
*G01B 9/02* (2006.01)
(52) U.S. Cl. ........................................ 356/450
(58) Field of Classification Search .................. 356/128, 356/129, 450, 517; 435/288.7
See application file for complete search history.

(56) References Cited

U.S. PATENT DOCUMENTS

| | | | |
|---|---|---|---|
| 6,381,025 B1 | 4/2002 | Bornhop et al. | |
| 6,381,925 B2 | 5/2002 | Rejcek et al. | |
| 6,809,828 B2 | 10/2004 | Bornhop et al. | |
| 7,130,060 B2 | 10/2006 | Bornhop et al. | |
| 7,172,897 B2 | 2/2007 | Blackburn et al. | |
| 7,835,013 B2 * | 11/2010 | Jones et al. | 356/517 |
| 2006/0012800 A1 | 1/2006 | Bornhop et al. | |
| 2006/0263777 A1 | 11/2006 | Tong | |
| 2007/0012777 A1 | 1/2007 | Tsikos et al. | |
| 2007/0195321 A1 | 8/2007 | Soussaline et al. | |

FOREIGN PATENT DOCUMENTS

| | | |
|---|---|---|
| WO | WO 2004/023115 A1 | 3/2004 |
| WO | WO 2006/047408 A2 | 5/2006 |
| WO | WO 2006/047408 A3 | 6/2006 |
| WO | WO 2008/144496 A1 | 11/2008 |

* cited by examiner

*Primary Examiner* — Michael A Lyons
(74) *Attorney, Agent, or Firm* — John Storella; Quine Intellectual Property Law Group, P.C.

(57) ABSTRACT

This invention provides an interferometric detection device configured to maintain a temperature of a sensing area to within 20 m° C. of a first target temperature and to maintain a temperature of the medium within 500 m° C. of a second target temperature The device can do so under conditions in which ambient temperature changes from 0.1° C. to 5° C. over 5 minutes.

31 Claims, 18 Drawing Sheets

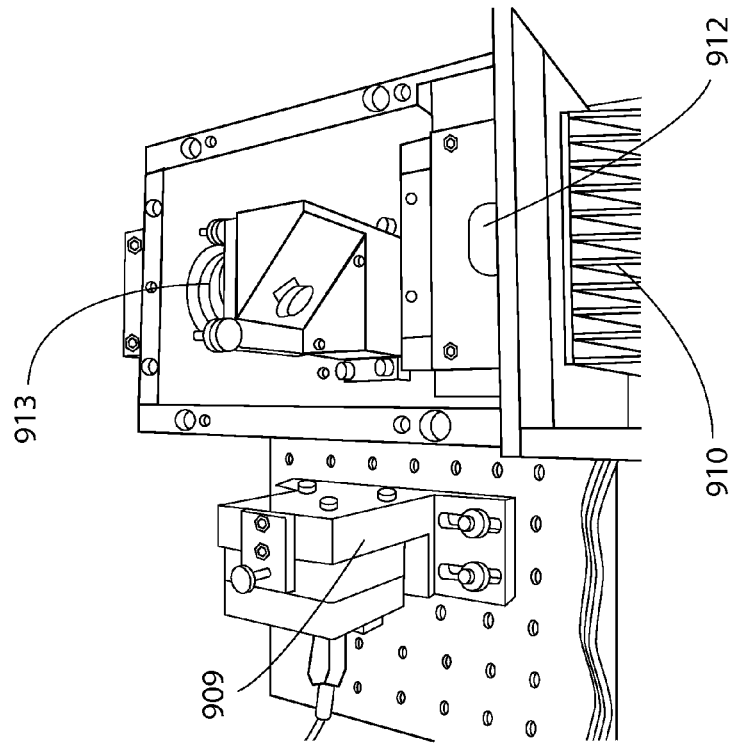
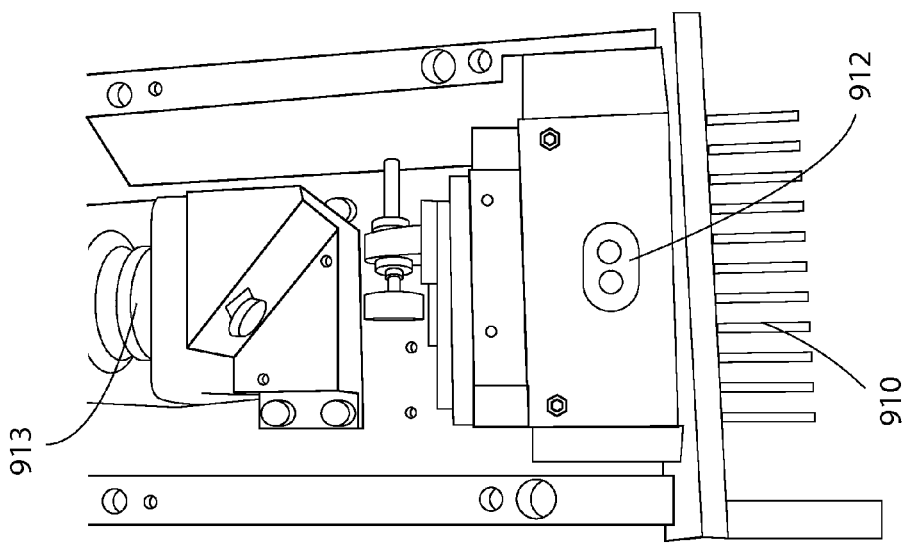
Fig. 9B
Fig. 9A

TEMPERATURE-STABLE INTERFEROMETER

CROSS-REFERENCE

This application claims the benefit of U.S. Provisional Application No. 61/012,752, filed Dec. 10, 2007, which application is incorporated herein by reference.

STATEMENT AS TO FEDERALLY SPONSORED RESEARCH

This invention was made with the support of the United States government under Contract number R01-EB-003537-03 by National Institutes of Health. The Government has certain rights in this invention.

BACKGROUND OF THE INVENTION

Rapid testing of a sample for an analyte, such as a biomarker, or the testing of molecular interaction in a sample is increasingly in demand, especially in the field of personal medicine. Traditionally, diagnostic tests, such as immunoassays, require both incubation time and complicated devices for reading the assay. Immunoassays also often require significant preparation of a sample holder or chip for binding an analyte to a surface. Recently, Back-Scattering Interferometry (BSI) has been validated for biochemical assays to measure the rate, concentration, and affinity of biomolecular interactions, such as protein-protein, antibody-antigen interactions, small molecule-protein interactions, DNA-DNA and DNA-protein binding. BSI devices and methods are described, for example, in U.S. Pat. Nos. 6,381,925; 6,381,025; 6,809,828 and 7,130,060; international applications WO 2004/023115, WO 2006/047408 and WO 2008/144496; and U.S. patent publication U.S. 2006-0012800.

Back Scattering Interferometry also has advantages of only requiring a small sample, such as 1 microliter, to conduct a biological assay. BSI can also offer label-free detection in a micro-chip format with picomolar sensitivity. BSI can be particularly valuable where trace sample requirements, extraordinary sensitivity, and/or free-solution analysis is required. Unlike other assays and biosensor techniques, BSI does not require significant knowledge of the interacting species and eliminates the need for finessing surface attachment chemistries. In addition to providing insight into basic cellular function, BSI has demonstrated potential to facilitate the development of therapeutics and diagnostics. Moreover, BSI can serve as the platform for many research, clinical diagnostic, and pharmacogenomic assays.

One of the shortcomings of many current BSI devices and methods is maintaining the temperature of the sample while it is being examined, while also maintaining the temperature of the device. A small change in temperature of the sample or the device can cause a change in a refractive index, which can lead to errors or non-specific measurements by an interferometer. It would be desirable in the art to have a BSI device that maintains the temperature of the device and the sample near or at a target temperature. Often, a BSI device utilizes a microfluidic chip to deliver the sample to a sensing area to be examined. Typically, the chip comprises channels of small dimensions, which can make it difficult for a user to interact with a chip and deliver a small sample to the chip. It would be desirable in the art to develop a microfluidic chip for use with BSI that can easily receive a sample from a user or sample delivery device, such as a pipette. The invention disclosed herein addresses some the issues in creating a reusable, stable interferometer.

SUMMARY OF THE INVENTION

In one aspect this invention provides an interferometric detection device comprising a microfluidic chip with a sensing area, wherein the temperature of said sensing area is maintained within 20 m° C. of a target temperature under conditions in which ambient temperature changes from 0.1° C. to 5° C. over 5 minutes. In one embodiment the device further comprises an optical enclosure containing a medium through which an optical train travels to the chip, wherein the temperature of the medium is maintained within 500 m° C. of a target temperature under conditions in which ambient temperature changes from 0.1° C. to 5° C. over 5 minutes. In another embodiment the device further comprises a coherent light source positioned to direct a beam along said optical train toward said sensing area to generate a back-scattering light pattern. In another embodiment the device further comprises a photodetector configured to detect the back-scattering light pattern. In another embodiment the device further comprises an optical bench, wherein said microfluidic chip, said optical enclosure, said coherent light source, and said photodetector are attached to said optical bench, and wherein said optical bench provides vibrational damping. In another embodiment the device further comprises an electronics compartment comprising: circuitry for a temperature control unit; and circuitry for an instrument control unit, wherein the instrument control unit communicates with at least one of the coherent light source and the photodetector. In another embodiment the device further comprises a dam that thermally separates the optical bench from said electronics compartment. In another embodiment the temperature control unit comprises: a plurality of temperature sensors that measure at least one of: the temperature at a surface of the chip, the temperature within the optical enclosure, the temperature within the optical assembly, the ambient temperature, and the temperature within the electronics assembly; a first heat pump configured to transfer heat to or from said medium inside the optical enclosure; a second heat pump configured to transfer heat to or from a surface of the chip; and circuitry comprising an electrical connection configured to regulate temperature at the chip surface and of the medium inside the optical enclosure by receiving measurements from the temperature sensors and to regulating heat flow in the heat pumps as a function of the measurements. In another embodiment the heat pump and the second heat pump are Peltier devices.

In another aspect this invention provides an interferometric detection device comprising: an optical assembly comprising: i) a microfluidic chip with at least one microfluidic channel with a sensing area; ii) a coherent light source positioned to direct a beam toward the microfluidic channel wherein the path of the beam defines an optical train and generates a back-scattering light pattern; and iii) a photodetector configured to detect the back-scattering light pattern; and an electronics assembly comprising circuitry for a temperature control unit configured to control the temperature of a medium through which the optical train travels and the temperature of the microfluidic chip; wherein said optical train and chip are thermally separated from said photodetector and said optical assembly is thermally separated from said electronics assembly. In one embodiment the temperatures are controlled by at least one heat pump. In another embodiment the heat pump is a Peltier device. In another embodiment the electronics assembly further comprises circuitry for an instrument control unit, wherein the instrument control unit communicates with at least one of the coherent light source and the photodetector. In another embodiment the sensing area has a volume of no more than 10 nl. In another embodiment the device further comprises an optical enclosure that thermally separates the optical train from the photodetector, wherein the enclosure comprises means to allow the back-scattering light pattern to reach the photodetector. In another embodiment the temperature of said medium through which the optical train travels is maintained within 500 m° C. of a target temperature. In another embodiment the temperature of said chip is maintained within 20 m° C. of a target temperature.

In another aspect this invention provides an interferometric detection device comprising an optical enclosure containing a microfluidic chip with a sensing area and a medium through which an optical train travels to the sensing area, wherein the temperature of the medium is maintained within 500 m° C. of a target temperature by a computer-controlled thermal regulation system.

In another aspect this invention provides a microfluidic system comprising: a microfluidic chip comprising a microfluidic channel opening onto a chip inlet and a chip outlet, wherein the channel comprises: a sensing area having a volume between about 0.1 nl and about 10 nl; and a fluid delivery area adapted to deliver fluid to the sensing area; and a fluidic adaptor comprising a fluidic adaptor channel opening onto an adaptor inlet and an adaptor outlet, wherein the adaptor inlet is adapted to mate with a pipette tip adapted to deliver between 0.1 microliter and 10 microliters of fluid and the outlet is mated with the chip inlet, wherein said adaptor channel and the fluid delivery area have a volume of no more than 1 microliter and a length of no more than 7 millimeters.

In another aspect this invention provides a microfluidic device that can receive between 0.1 and 10 microliters of a sample having an analyte at a picomolar concentration, and deliver at least a portion of the sample through a microfluidic channel to a sensing area with a change in analyte concentration of no more than 5%. In another embodiment the volume of said sensing area is less than 10 nanoliters.

In another aspect this invention provides a method comprising: operating an interferometric device that detects a diffraction pattern in a microfluidic chip comprising maintaining the temperature of the chip to within 20 m° C. (preferably within 5 m° C.) of a target temperature under conditions in which ambient temperature changes from 0.1° C. to 5° C. over 5 minutes.

In another aspect this invention provides a method comprising delivering between 0.1 microliter and 10 microliters of a sample having an analyte having a concentration of no more than 100 picomolar to a sensing area of a microfluidic chip and measuring the concentration of the analyte by interferometry. In one embodiment the difference in concentration of the analyte between delivery and the sensing area is no more than 5%.

In another aspect this invention provides a method of maintaining temperature within an interferometer comprising: detecting temperature (1) at a sensing area of a microfluidic chip within the interferometer, (2) of a medium within an enclosure through which an optical train travels between a coherent light source and the sensing area and (3) of the ambient environment; regulating activity of a first heat pump in thermal contact with the microfluidic chip and a second hear pump in thermal contact with the medium as a function of the measured temperatures.

In some instances, a method for determining a refractive index of a liquid comprises: providing a liquid to the sensing area of a device as described herein and detecting movement of a fringe pattern generated by interferometric analysis with the device to indicate a change in the refractive index of the liquid. The liquid can comprise a first and second biochemical species. Using the methods as described herein, the interaction of the first and second biochemical species can be monitored by detecting a change in the refractive index of the liquid over time as determined by interferometry utilizing a device described herein. In an embodiment, the first and second biochemical species are selected from the group comprising: complimentary strands of DNA, complimentary proteins and antibody-antigen pairs. In another embodiment, the liquid comprises a ligand and one or more receptors. A method herein can be used to determine whether the ligand binds with the one or more receptors by monitoring changes in the refractive index of the liquid. In yet another embodiment, a method herein can be used to analyze a label-free hybridization reaction in the liquid.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 9A shows the interior components of an interferometric device comprising a heat pump (910), a sample delivery aperture (912), and optics for light delivery (913).

FIG. 9B shows contents of an optical compartment comprising optics (913) for light delivery to a chip and reflection to a photodetector (909), a heat pump (910), a sample delivery aperture (912), and.

DETAILED DESCRIPTION OF THE INVENTION

Figure 1:
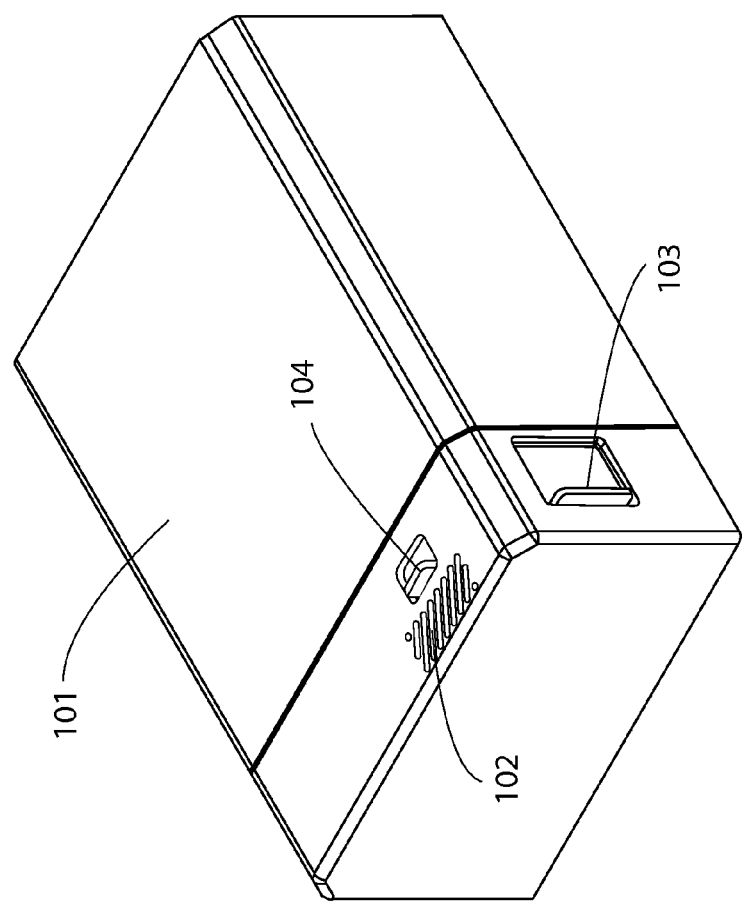
FIG. 1 shows the housing (101) of an interferometric detection device comprising a vent (102), an opening for sample delivery (104), and an opening for access to a microfluidic chip cartridge (103).

A device and method are provided for interferometric measurements of analyte interactions in a sample. The device and method can be applicable for a variety of fields, such as biological marker identification and quantification, and chemical reaction monitoring. Also, small samples, for example, on the order of a microliter, containing an analyte to be measured by a device or method of the invention can be evaluated. In addition, due to the properties of the interferometric detection, the analyte concentration in a sample can be determined from a free sample without labeling the analyte with another molecule, compound or dye. Furthermore, the assays can detect analytes in the picomolar range (i.e., 1 picomolar to 1000 picomolar) and below in samples in the microliter range (0.1 to 10 microliters).

The device and methods of the invention disclosed herein have numerous applications including, but not limited to, the observation and quantification of molecular interactions, molecular concentrations, bioassays, and detection for CE (capillary electrophoresis), CEC (capillary electrochromatography) and FIA (flow injection analysis), as well as cell sorting/detection by scatter, ultra micro calorimetry, flow rate sensing, and temperature sensing.

A typical Back Scattering Interferometry (BSI) device comprises a simple optical train employing a He/Ne laser, a microfluidic channel, and a photodetector. BSI may have significant advantages over ELISA as well as label-free, molecular interaction biosensor approaches such as microcalorimetry, surface plasmon resonance, and other waveguide technologies. A BSI system can demonstrate picomolar sensitivity, using very small sample volumes (<2 microliters), while requiring little prior knowledge of the molecular interactors. BSI can be used to measure molecular interaction kinetics and performs quantitative, end-point assays. BSI technology can be used to discover new biomarkers, rapidly develop assays, and run routine, quantitative molecular interaction-based assays in seconds at picomolar concentrations in either free-solution or surface-bound, label-free modes.

In an aspect of the invention, an interferometric detection device is disclosed that comprises a microfluidic chip with a sensing area, wherein the temperature of said sensing area is maintained within 20 m° C., within 10 m° C., within 5 m° C., within 1 m° C. or within 0.5 m° C. of a target temperature under conditions in which ambient temperature changes up to 5° C. over 10 seconds, over 30 seconds, over 1 minute or over 5 minutes (or any combination of these). In an embodiment, the ambient temperature changes from 0.1° C. to 5° C. over 5 minutes while the sensing area is maintained within 20 m° C., within 10 m° C., within 5 m° C., within 1 m° C. or within 0.5 m° C. of a target temperature. In other embodiments, the ambient temperature changes from 0.01° C. to 10° C. over 10 seconds, over 30 seconds, over 1 minute or over 5 minutes. Typical target temperatures are between 15° C. and 37° C., typically about 25° C. The sensing area can be an area or volume of a microfluidic chip, wherein the sensing area is the portion of the chip that is exposed to a coherent light source to provide back-scattering light to a photodetector for the measurement of at least one analyte in a sample. The refractive index of the sample containing the analyte can change with temperature, altering the results of the measurements. When temperature change occurs somewhat rapidly, for example, in the course of one test or a series of related tests, the temperature change can cause error in the measurement results of an interferometric device. For example, a temperature change due a door opening in a room can change the results of a measurement. In an embodiment, a device of the invention is capable of maintaining the temperature of the microfluidic chip within 20 m° C. of a target temperature for measurement of an analyte in a sample.

Temperature stability of the optical train and of the chip is achieved by in the following way. The heat generating components of the device, in particular electrical circuitry, are thermally isolated from the optical assembly. In one embodiment, this is done by providing a compartment containing the optical assembly that is separated from heat generating electrical circuitry by a thermal dam—a wall of material that insulates the optical assembly from the electrical components. Another compartment also is provided that thermally isolates the portion of the optical train that travels from a coherent light source, e.g., a laser, to the sensing area of the microfluidic chip. Furthermore, this second compartment is itself temperature controlled with a heat pump, such as a peltier device, to achieve a target temperature, so that the medium through which the beam travels, e.g., air, remains at a constant temperature, thereby diminishing fluctuations in the optical train. Another heat pump controls the temperature of the chip. The device is further provided with temperature feed-back mechanisms that measure temperature at various points in the device and the ambient temperature, and regulate the activity of the heat pumps as a function of the measured temperatures. Temperatures are measured, for example, at the chip-heat pump interface (e.g., at the heat spreader connected to the peltier device), in the temperature integrator compartment through which the optical train travels from the coherent light source to the chip, in the compartment containing the optical assembly outside of the integrator box, and the ambient temperature. An electronic control system can control temperature as follows. Temperature measurements from optical enclosure are taken by temperature sensors. These measurements are sent to a processor. The processor executes an algorithm. The algorithm can determine the difference between the target temperature and the actual temperature measured in the at the chip surface and/or in the optical compartment. Based on this difference, the control system then sends an instruction to the various temperature control mechanisms, such as the peltier device, to increase or decrease temperature in the direction of the target temperature.

As would be readily understood by one of skill, the term "back-scatter" is generally used to describe the origin of the light rays that form the interference pattern. On the basis of theoretical analysis of the origin of the interference pattern presented herein, the term reflection can be used as well, but the phenomenon referred to by these terms is in each case the same.

In an embodiment, a device of the invention can further comprise an optical enclosure containing a medium through which an optical train travels to the chip, wherein the temperature of the medium is maintained within 500 m° C., within 100 m° C., 50 m° C., 20 m° C., 10 m° C. or 5 m° C. of a target temperature under conditions in which ambient temperature changes by some degree for up to 10 seconds, over 30 seconds, over 1 minute or over 5 minutes (or any combination of these). In an embodiment, the ambient temperature changes from 0.1° C. to 5° C. over 5 minutes while the medium is maintained within 20 m° C., within 10 m° C., within 5 m° C., within 1 m° C. or within 0.5 m° C. of a target temperature. In other embodiments, the ambient temperature changes from 0.01° C. to 10° C. over 10 seconds, over 30 seconds, over 1 minute or over 5 minutes. Typical target temperatures are between 15° C. and 37° C., typically about 25° C. The temperature may be maintained within the optical enclosure or with tubes inside the optical enclosure if these are used. When performing an interferometric measurement on a sample, the temperature in the room or laboratory where the measurement is made can fluctuate significantly. As the temperature of the room changes, when the medium surrounding the optical train is air, the refractive index of the medium can change with the temperature of the room. This can lead to measurement errors using an interferometric device. A device of the invention capable of maintaining the temperature of the medium through which an optical train travels can reduce the measurement error of the device during use. Measurement error can be reduced by a temperature-stable interferometer of the invention by up to 10%, 20%, 30%, 40%, 50%, 60%, 70%, 80%, or 90%.

In measurements of refractive index (n), the primary source of noise is thermal sensitivity. For most cases involving fluids, n has a relatively high thermal coefficient (dn/dT), requiring very precise temperature stabilization of the system. As an example, dn/dT for $H_2O$ is on the order of $8 \times 10^{-4}$ °$C.^{-1}$, so at an analytically useful detection limit for $\Delta n$, the temperature-induced signal corresponds to a change in T of $1 \times 10^{-3}$ ° C. Therefore, thermal stability of the system must be maintained at the millidegree centigrade label, to determine n.

Conversely, as discussed previously, thermal noise in refractive index measurements can be used to the advantage of the user. For example, thermal sensitivity can be used to determine minute temperature changes in small volume samples or sample streams and even protein folding. The relationship between dn and dT is linear. Therefore, back-scattering interferometry can be used to measure thermal changes at a microdegree centigrade level and to determine dn/dT for fluids.

An interferometric device of the invention can comprise a coherent light source positioned to direct a beam along an optical train toward a sensing area on a microfluidic chip to generate a back-scattering light pattern. The sensing area of the chip can be filled with a sample, such as liquid sample. The liquid sample can be a biological sample, for example, a bodily fluid, such as blood or saliva. When the sensing area is filled with a sample, the beam is directed to the sample and a back-scattering light pattern is generated based on the contents and/or composition of the sample.

A photodetector can be configured and incorporated into a device of the invention to detect a back-scattering light pattern from a sensing area on a microfluidic chip. The photodetector can detect a back-scattering light pattern generated from a sample in the sensing area of the chip, wherein the pattern is based on the contents and/or composition of the sample. In an embodiment, qualitative and quantitative measurements are performed by forming molecular complexes, such as antibody antigen. Detection can be performed in a similar manner to an ELISA measurement, only a label on the antibody (in the case of an antigen based assay) is not used. In an embodiment, the photodetector detects a qualitative or quantitative value of an analyte in a liquid sample, for example, the amount of glucose in a blood sample.

The photodetector can be one of any number of image sensing devices, including a bi-cell position sensor, a linear or area array CCD or CMOS camera and laser beam analyzer assembly, a slit-photodetector assembly, an avalanche photodiode, or any other suitable photodetection device. The back-scattered light comprises interference fringe patterns that result from the reflective and refractive interaction of the incident laser beam with the walls of the sensing area and the sample. These fringe patterns include a plurality of light bands whose positions shift as the refractive index of the sample is varied, for example, through compositional changes. In an embodiment, the photodetector detects the backscattered light and converts it into one or more intensity signals that vary as the positions of the light bands in the fringe patterns shift. For fringe profiling, the photodetector can be mounted above the chip at an approximately 45° angle thereto. Fringe profiling can also be accomplished by detecting the direct backscatter. In an embodiment, the fringes off can be profiled in direct backscatter configuration and direct them onto the camera which is at 90° from the beam, in this way, the packaged device can remain small while maximizing the resolution for measuring a positional shift, for example, the effect of angular displacement.

The intensity signals from the photodetector can be fed through an instrument control unit into a signal analyzer for fringe pattern analysis for determination of the refractive index or an RI related characteristic property of a sample in the sensing area of the microfluidic chip. The signal analyzer can be a computer (for example, a PC) or a dedicated electrical circuit. Preferably, the signal analyzer includes the programming or circuitry necessary to determine from the positional shift of the formed fringes, the RI or other characteristic properties of the sample to be determined, such as temperature or flow rate, for example.

A coherent light source can be directed onto a sensing area of a microfluidic chip such that the light beam is incident on the channel to generate backscattered light through reflective and refractive interaction of the light beam with the sensing area interface and the sample, the backscattered light comprising interference fringe patterns including a plurality of spaced light bands whose positions shift in response to the refractive index of the sample. Positional shifts in the light bands relative to a baseline or a reference value can then be detected by a photodetector and computed using a processor, such as a PC. The device can provide a signal (for example, positional shifts in the light bands) that is proportional to abundance of the analyte.

Housing

Figure 2B:
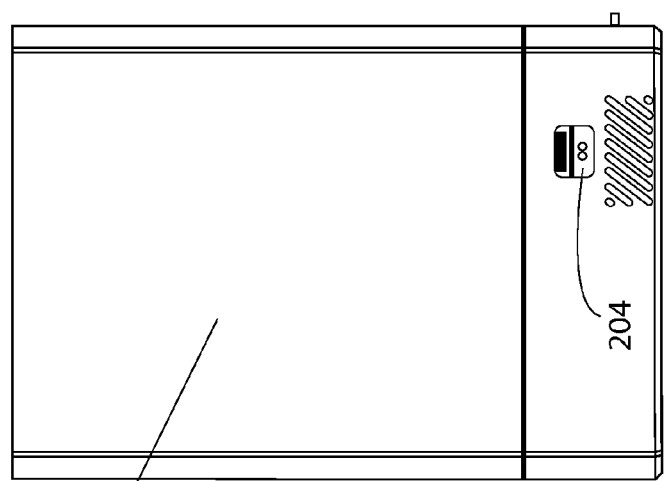
FIG. 2B shows the top view of a housing (201) of an interferometric detection device comprising an opening for sample delivery (204), and an opening for access to a microfluidic chip cartridge.
Figure 2A:
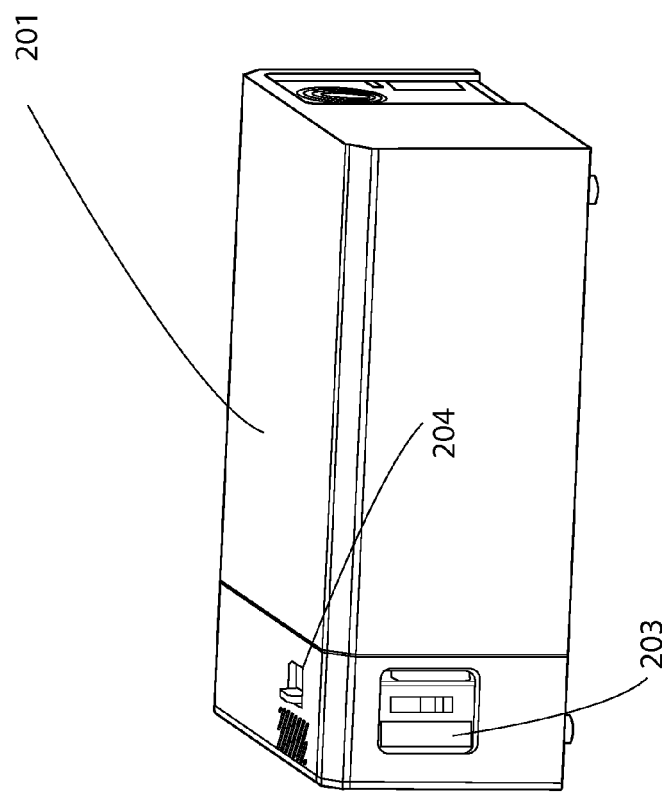
FIG. 2A shows the side view of a housing (201) of an interferometric detection device comprising an opening for sample delivery (204), and an opening for access to a microfluidic chip cartridge (203).
Figure 3:
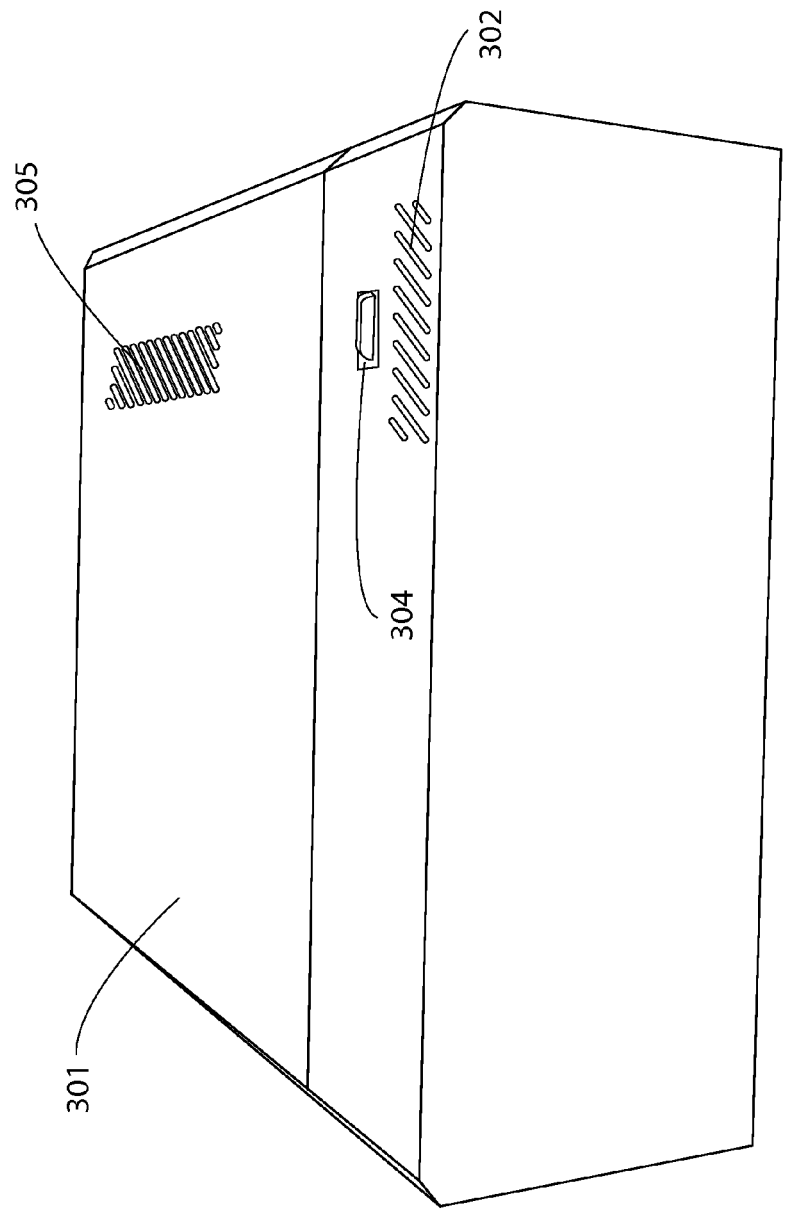
FIG. 3 shows the housing (301) of an interferometric detection device comprising at least two vents (302, 305), an opening for sample delivery (304).

FIG. 1 illustrates an exemplary interferometric detection device of the invention with a housing (101) comprising a vent (102), an opening for sample delivery (104), and an opening for access to a microfluidic chip cartridge (103). The housing (101) can cover the components of the device including an electronics compartment and an optical compartment. The housing (101) can be manufactured from a material that is a poor thermal conductor in order to thermally separate the compartments and components of the device from the ambient environment. The housing (101) can also comprise a thermal insulator. The vent (102) allows for heat to exit from the device for maintaining some of the internal components at a target temperature. In this example, the vent (102) is located over a heat sink coupled to a thermal subsystem for heating a microfluidic chip. The microfluidic chip can be removable front and insertable into the device through opening on the side of the device (103). In the example, a cover is also provided for thermally separating the chip and internal components from the ambient environment. The opening for sample delivery on the top of the device (104) in this example provides two access holes for inserting a pipette tip that can mate with an adapter channel which is in fluid communication with the microfluidic chip. In this way, a user can use a common pipette to deliver a small volume of sample (e.g., 0.1 microliter to 10 microliters, 0.5 to 5 microliters, 0.8 microliters to 3 microliters or about 1 microliter) into the chip and device of the invention for interferometric detection of an analyte in the sample. Alternatively, a robotic system employing pipettes can interface with the device and automatically introduce sample. The opening (104) can be of any size in shape. In an embodiment, the opening for sample delivery (104) allows for an automated system to deliver a sample to the device. In another embodiment, the sample delivery opening (104) can mate with a common lab device such as a reaction vial. The openings (103, 104) of the device for the microfluidic chip and sample delivery can be located on any side of the device. Preferably, the openings (103, 104) are located with respect to each other, such that the sample from the sample delivery will enter the microfluidic chip without any additional movement or transportation. In an embodiment, the openings (103, 104) are established at an accepted pitch, such as 9 mm pitch, to insure compatibility with industry standard robotics. FIG. 2A shows the side view of the housing (201) of an embodiment of the interferometric detection device of the invention comprising an opening for sample delivery (204), and an opening for access to a microfluidic chip cartridge (203). FIG. 2B shows the top view of the housing (201) of an interferometric detection device comprising an opening for sample delivery (204), and an opening for access to a microfluidic chip cartridge. FIG. 3 shows the housing (301) of an interferometric detection device comprising at least two vents (302, 305), an opening for sample delivery (304). In the exemplary device in FIG. 3, on the vent is located over a heat sink in thermal contact with a heat pump for maintaining the temperature of the microfluidic chip within 5 m° C. of a target temperature. The other vent is located above a coherent light source, which when operated can generate heat if not properly ventilated.

Optical Bench

In an embodiment, a device of the invention comprises an optical bench, wherein a microfluidic chip, an optical enclosure, a coherent light source, and a photodetector are attached to the optical bench, and wherein the optical bench provides vibrational damping. Another source of error of a measurement with an interferometric device is the movement of one or more parts of the device. By mounting all of the optical components on an optical bench, the optical components can move together and, as such, the optical train and the backscattering light pattern may remain the same regardless if the device makes any small movements. The vibrational damping of the optical bench can be achieved by rubber feet mounted on the bottom of the optical bench. In another embodiment, vibrational damping is provided by springs attached to the optical bench. In another embodiment, the optical bench can be mounted on a shock absorbing apparatus. Any other device, apparatus, or method for that is practical for vibrational damping of the optical bench can be used as would be obvious to one skilled in the art.

The optical bench can have a means for dampening any movement or vibration of the components attached to the bench. As such, if movement does occur, all the components on the bench can move together as to not interfere with the measurements of an analyte concentration in a sample.

Figure 6:
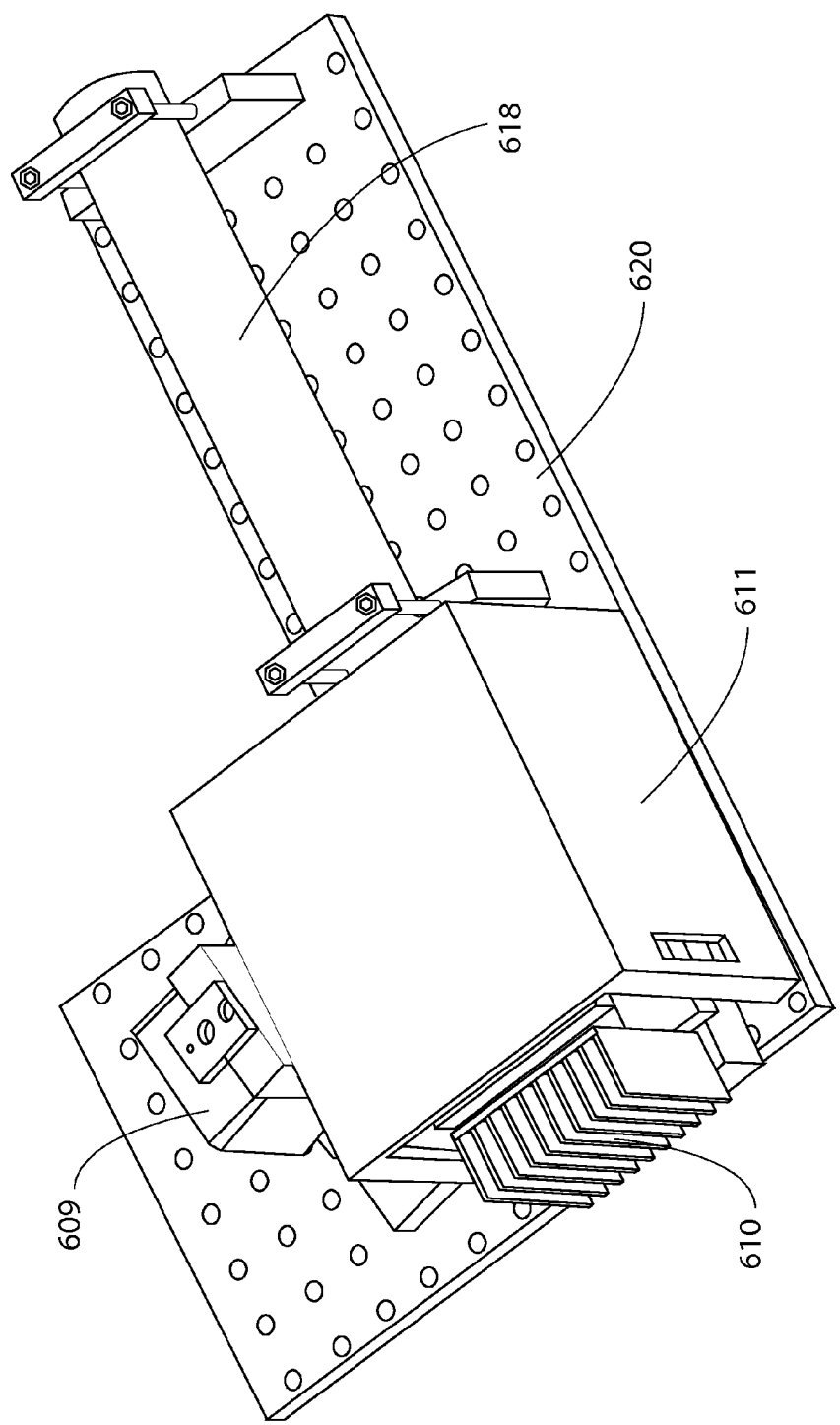
FIG. 6 shows the interior components of an interferometric device, in particular an optical assembly comprising a a coherent light source (618), an optical enclosure (611), a heat pump (610) and a photodetector (609), all of which are attached to an optical bench-board (620).
Figure 10:
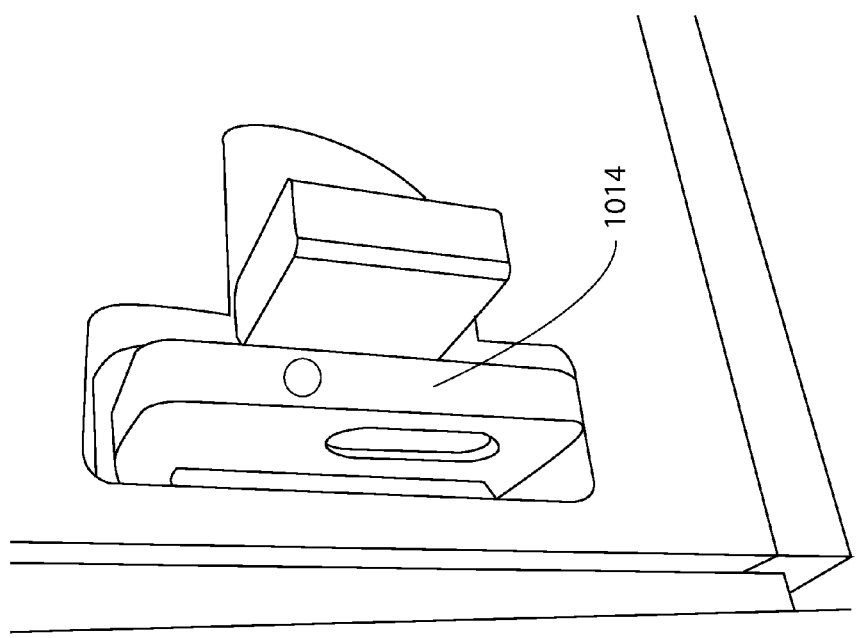
FIG. 10 shows the interior components of an interferometric device comprising a microfluidic chip cartridge (1014).

FIG. 6 demonstrates the interior components of an interferometric device attached to an optical bench, including a photodetector (609), a heat pump (610), an optical enclosure (611), and a coherent light source (618). The components can be located anywhere on the optical bench, such that they are arranged to work together. The optical enclosure (611) encloses the optical train of the device as referred to by the path of the light within the device. The coherent light source (618) sends a light beam into the optical enclosure (611) to the microfluidic chip which is in thermal contact with the heat pump (610). The light beam is incident with a sample contained within the sensing area of the chip and the backscattering light pattern is detected by the photodetector (609). Optics can be contained within the optical enclosure (611). As shown in FIG. 6, the optical enclosure (611) along with the heat pump (610) encloses the microfluidic chip. The optical enclosure (611) thermally separates the medium surrounding the optical train from the rest of the device in order for the temperature control unit to maintain the temperature of the medium within 500 m° C. of a target temperature. The optical enclosure (611) is also shown with an aperture in one side to provide access for moving a microfluidic chip into and out of the enclosure (611). FIG. 10 demonstrates the aperture for inserting a microfluidic chip and the microfluidic chip holder (1014) into the optical enclosure.

Figure 8:
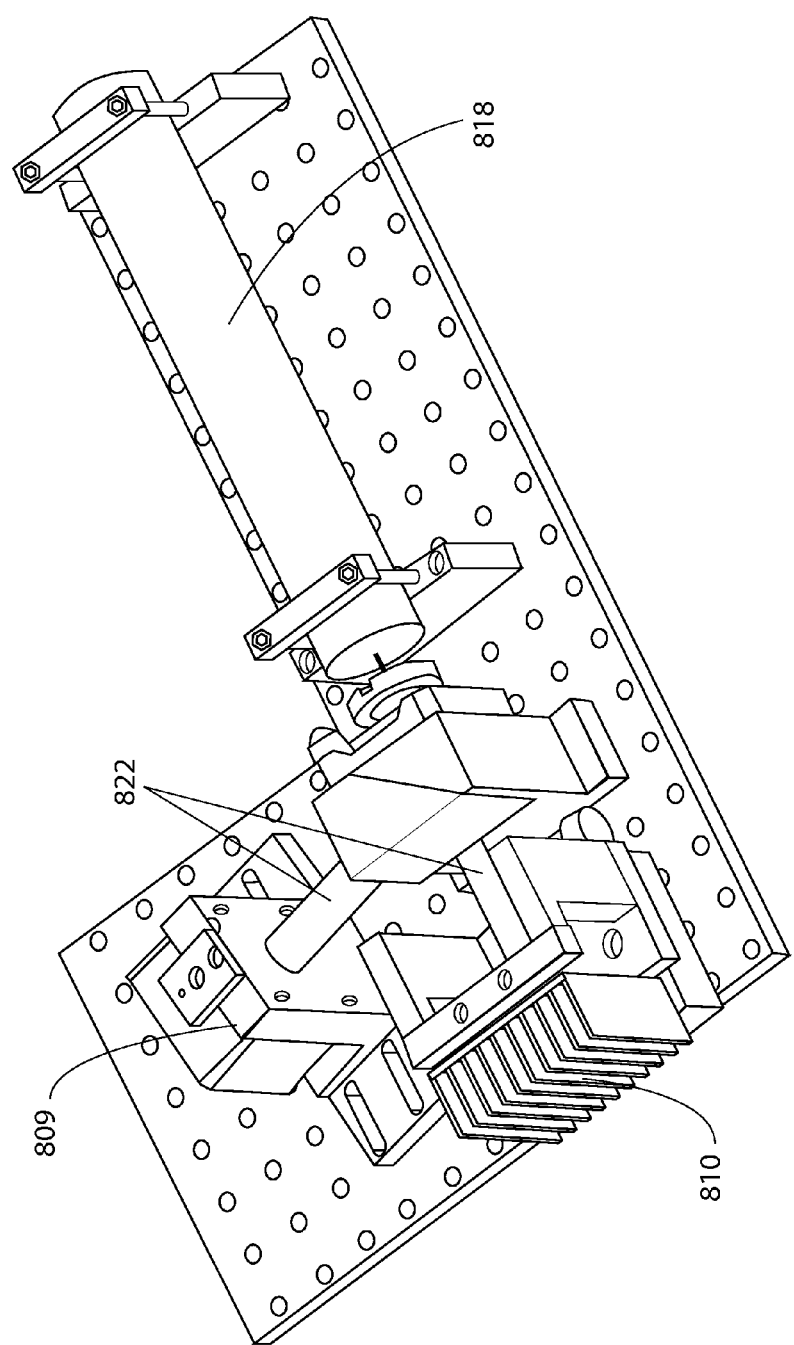
FIG. 8 shows the interior components of an interferometric device comprising an optical assembly comprising a coherent light source (818), optical unit (813), openings for sample delivery into the chip (804), photodetector (809), a heat pump (810), and, wherein the device also comprises enclosed pipes (822) to insure against unwanted particulates and heat changes through the coherent light.

Referring to FIG. 8, in one embodiment coherent light source (e.g., laser) (818) directs light through optical unit (813) comprising a beam splitter to two channels of chip located under ports (804). Scattered light is reflected back and directed by a minor in optical unit (813) to detector (809). The chip is heated and cooled by heat pump (810). The unit is shown without the optical enclosure cover.

This figure also indicates the enclosed light pipes to insure against unwanted particulates and heat waves through the laser beams. This is important to minimize noise in the measurement process and protect against unwanted thermal impacts upon local media (air) refractive index, as well as introduction of particulates (dust) which would scatter the beam.

In an embodiment, attached to the optical bench is a coherent light source, optics, a heat pump to change the temperature of a microfluidic chip, and a photodetector. The heat pump can be any device capable of heating a solid, for example, the microfluidic chip. A Peltier device, or thermoelectric heat pump, is an example heat pump that can be incorporated into a device of the invention. The optics on the optical bench can be any material that is capable of directing a pattern of photons, such as the back-scattering of a coherent light source after it has illuminated a sample containing an analyte. The optics can be a mirror, a dichroic mirror, prism, beam splitter (to direct the beam to two or more channels of the microfluidic chip) or fiber optics. The optics can also be connected to a device that is capable of positioning the optics in different orientations either manually, automatically, or according to commands from a user. Examples of coherent light sources for use with the invention include, but are not limited to, a laser, for example a He/Ne laser, a VCSEL laser, and a diode laser. The coherent light may be coupled to the site of measurement by known wave-guiding or diffractive optical techniques or may be conventionally directed to the measurement site by free space transmission.

An interferometric detection device of the invention can comprise a laser or other source of coherent light, which is preferably a low power (for example, 3-15 mW) laser (for example, a He/Ne laser). As with any interferometric technique for chemical analysis, the devices and methods of the invention benefit from many of advantages lasers provide, including high spatial coherence, monochromaticity, and high photon flux. The beam can be directed directly to a sensing area on the microfluidic chip or to a mirror that is angled with respect to the plane of propagation of the laser beam, wherein the mirror can redirect the light onto the sensing area.

In an embodiment, the coherent light source generates an easy to align collimated laser beam that is incident on a sensing area of the microfluidic chip for generating the backscattered light. The backscattered light comprises interference fringe patterns that result from the reflective and refractive interaction of the incident laser beam with the sensing area walls and the sample in the sensing area. These fringe patterns include a plurality of light bands whose positions shift according to the refractive index of the sample, for example, due to the composition of the sample. The photodetector can detect the backscattered light and convert it into intensity signals that can be used to determine the refractive index (RI), or an RI related characteristic property, of the sample. For example, the RI of a sample with a certain concentration of analyte in the sample can be slightly different than the RI of a sample where the analyte is present in the sample in a different concentration. A signal analyzer, such as a computer or an electrical circuit, can be employed to analyze the photodetector signals and determine the characteristic property of the sample.

Optical Enclosure

A device of the invention can comprise an optical enclosure that thermally separates the optics, a microfluidic chip in thermal contact with the heater, and the optical train through which the coherent light source travels from the rest of the device. The optical enclosure has an aperture that can be covered to provide to information from the back-scattering of the light to a photodetector. The photodetector can be located next to, near, in or within optical contact of the enclosure, for example, through fiber optics. A heat pump can be used to control the temperature of the medium within the optical enclosure. In an embodiment, the heat pump is a Peltier device. The medium within the optical enclosure can be maintained within 500 m° C. of a target temperature to prevent errors in the measurement of analyte concentration in a sample. If the temperature of the medium changes, the measurement can change because the refractive index of the medium changes with temperature. In an embodiment, the medium is air. The medium can also be any gas or liquid through which a coherent light source may travel, as would be obvious to one skilled in the art. In another embodiment, the medium in the optical enclosure is a vacuum. In another embodiment, the optical enclosure can be pressure regulated to maintain the pressure within the enclosure at or near a target pressure, for example, 1 atm.

In an embodiment, the optical enclosure has a substantial amount of heat content, using appropriately chosen materials with a chosen specific heat value. As the temperature of the room fluctuates, the optical enclosure can be somewhat impervious to that change, because it has considerable stored heat. Further, when the optical enclosure does shift in temperature, for example, during prolonged exposure to a constant thermal change, then the temperature change can be seen over a long time constant, for example, many minutes. As such, it will not perturb the measurement process.

A device of the invention with an optical enclosure can optically separate the optical train and at the same time provide a thermal integrator which is resistant to transient temperature changes because it has stored heat. Examples of material suitable for an optical enclosure of the invention include, but are not limited to, anodized aluminum (various grades) and stainless steel (various alloys).

In another embodiment, the temperature of the optical enclosure can be actively controlled in response to temperature changes in ambient temperature as sensed by a sensor, and/or changes of temperature of the electronics compartment, and/or a desired set of temperatures of the chip.

The optical enclosure thermally separates the optical train and the medium through which the optical train travels from electronics used to control or power a photodetector, a heat pump, a coherent light source, or any other electronics in the vicinity of the enclosure. The optical enclosure may also comprise an opening through which a microfluidic chip or microfluidic chip holder can be inserted into the enclosure. In another embodiment, the optical enclosure may comprise a hole or series of holes to deliver a sample to a microfluidic chip within the enclosure.

In addition to insulating the optical train from temperature changes in the optical compartment, the optical enclosure also comprises a heat pump which regulates the temperature of the medium through which the coherent light travels. This provides another level of stability for the system.

Figure 7:
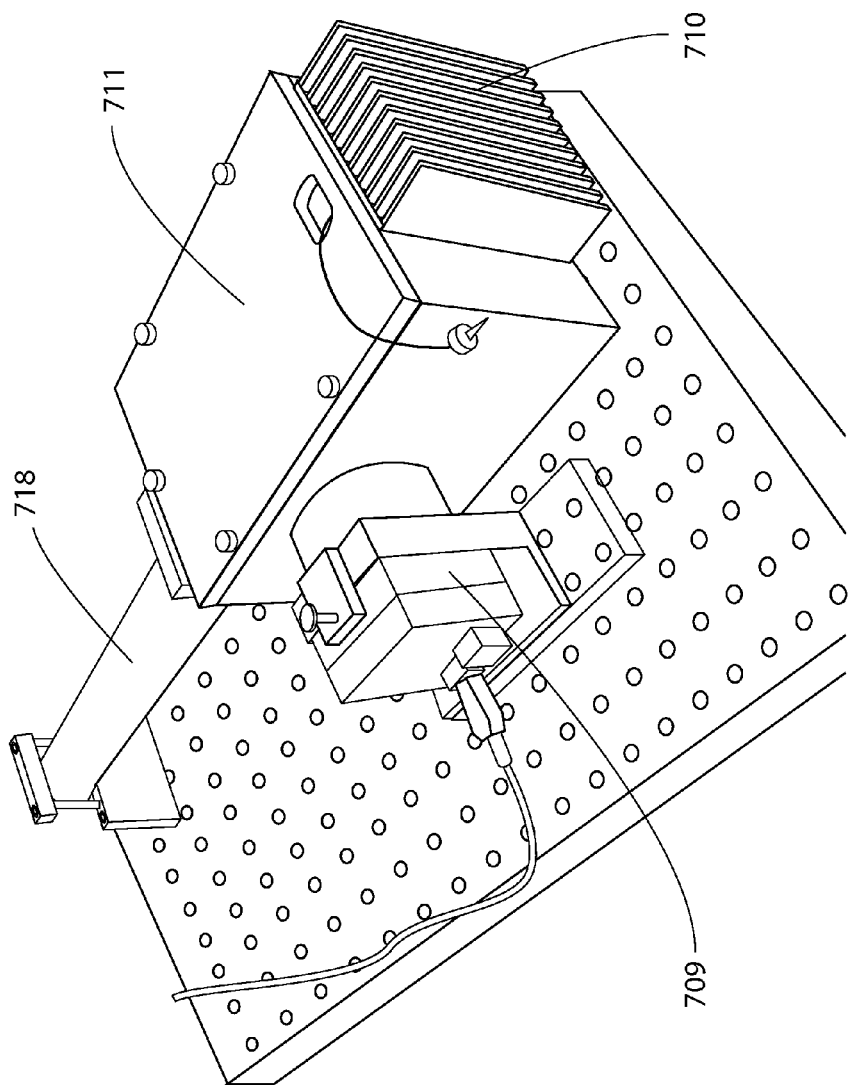
FIG. 7 shows the interior components of an interferometric device comprising of an interferometric detection device comprising a photodetector (709), a heat pump (710), an optical enclosure (711), and a coherent light source (718).

FIG. 7 shows the interior components of an interferometric device comprising of an interferometric detection device comprising a photodetector (709), a heat pump (710), an optical enclosure (711), and a coherent light source (718). The components are shown attached to an optical bench. The optical enclosure (711) is shown with a small aperture at the top to allow for a sample to be delivered to a microfluidic chip within the enclosure (711). The heat pump (710) and the optical enclosure (711) enclose the chip to thermally separate the chip from other parts of the device. The medium through which the optical train travels is also thermally separated from other parts of the device by the enclosure (711). FIG. 9A shows the interior components of an interferometric device comprising a heat pump (910), a sample delivery aperture (912), and optics for light delivery (913). FIG. 9B shows a photodetector (909), a heat pump (910), a sample delivery aperture (912), and optics for light delivery (913). In FIG. 9A-9B, a thermal subsystem comprising the heat pump (910) has a sample delivery aperture (912) located on top of the subsystem to provide a sample to the sensing area of a microfluidic chip in thermal contact with the subsystem. In a preferable embodiment, the sample delivery aperture (912) is aligned with the sample delivery opening of a housing covering the internal components of the device. In another preferable embodiment, the sample delivery aperture (912) is aligned to deliver a sample directly to an adapter channel configured to receive a pipette tip and deliver a sample to the sensing area of the chip. Preferably, less than 3 microliters of fluid are provided to the interferometer for quantitative detection of an analyte in a sample. In FIGS. 9A-9B the optics (913) within an optical enclosure of the exemplary device are shown. In this example the optics (913) are a mirror for directing the back-scattering light pattern to the photodetector (909).

Electronics Compartment

In an embodiment, the optical bench is thermally separated from an electronics compartment of the device. The optical bench is thermally separated in order to maintain the temperature of a medium through which the optical train travels within 500 m° C. of a target temperature. The electronics compartment can contain any electronics, circuitry, power source, or controller for operating the device. For example, the electronics compartment can contain circuitry for controlling the temperature of the chip and for controlling the temperature within the optical enclosure. The optical enclosure can also contain circuitry for operating instruments of the device, such as the coherent light source and the photodetector. The circuitry for a temperature control unit and/or the circuitry for the instruments can be circuit boards or computer boards. Wires to the instruments and thermal control systems (for example, temperature sensors and heat pumps) can originate in the electronics compartment and pass through over, or under the thermal dam that thermally separates the electronics compartment from the optical compartment.

In another embodiment, a device of the invention further comprises an electronics compartment comprising: a) circuitry for a temperature control unit; and b) circuitry for an instrument control unit, wherein the instrument control unit communicates with at least one of a coherent light source and a photodetector. The instrument control unit can be used for active control of any of the instruments of a device of the invention. The circuitry in the electronics compartment can connect with a computer external to the device that has a user interface. A user can access or actively control the instruments of the system through the user interface. The computer and the user interface can be contained or associated with the electronics compartment of the device.

In an embodiment, a device of the invention comprises a dam that thermally separates the optical bench from the electronics compartment. Often the electronics compartment can increase in temperature or be maintained at a higher temperature than the medium through which the optical train travels or the sensing area of the microfluidic chip. Without a dam, the temperature of the electronics compartment can influence the measurements by the photodetector because of the influence of temperature on the refractive index of a medium surrounding the optical train. A dam that separates the electronics compartment from the optical bench and optical train can make it easier to obtain temperature control of the measurement, which in turn, produces more accurate measurements. The dam can be made of any material that is a poor heat conductor. The dam can be made of an insulating material. In a preferable embodiment the dam is polycarbonate. Examples of materials suitable for use in the dam include, but are not limited to, plastics such as ABS, polystyrene, polyolefins, polyphenols, polyethylene, and the like.

A temperature control unit of the device can comprise all or some of the following: temperature sensors, heat pumps, circuitry, fans, and a computer or control system. In an embodiment, the temperature sensors are thermistors. In another embodiment, the temperature sensors are thermocouples. The temperature sensors can be any sensor for measuring temperature as would be obvious to one skilled in the art. In an embodiment, a heat pump heats a microfluidic chip of a device of the invention. The microfluidic chip may be in physical contact with the heat pump and/or within thermal contact of the heat pump or both. The microfluidic chip is heated to maintain the temperature of the sensing area within 5 m° C. of a target temperature. A temperature sensor may be on or immediately near the microfluidic chip to provide temperature feedback to the thermal control unit. The temperature feedback from the temperature sensor for control of the temperature of the chip can be utilized by the temperature control unit to operate the heat pump in thermal contact with the chip.

A temperature control unit of a device of the invention can comprise: a) a plurality of temperature sensors that measure at least one of: the temperature at a surface of the chip, the temperature within the optical enclosure, the temperature within the optical assembly, the ambient temperature, and the temperature within the electronics assembly; b) a first heat pump configured to transfer heat to or from said medium inside the optical enclosure; c) a second heat pump configured to transfer heat to or from a surface of the chip; and d) circuitry comprising an electrical connection configured to regulate temperature at the chip surface and of the medium inside the optical enclosure by receiving measurements from the temperature sensors and to regulating heat flow in the heat pumps as a function of the measurements.

The temperature sensors can be any temperature sensor capable of providing temperature feedback to the temperature control unit, such as thermocouples. The temperature control unit can be an active control system that receives temperature data from the temperature sensors and uses the data to control the heat pumps, which in turn control the temperature of a chip or of the medium surrounding the optical train in the optical enclosure.

Another heat pump can be utilized to control the temperature of the medium within the optical enclosure of a device of the invention. Changes of the temperature of the medium within the optical enclosure can alter measurements of the back-scattering of the coherent light source hitting the sensing area because at different temperatures the medium can have a different density which can affect the refractive index of the medium and, in turn, the measurements of the back-scattering by a photodetector. A temperature sensor within the optical enclosure can be used to deliver a feedback temperature to the temperature control unit for control of a heat pump for maintaining the temperature of the medium within the enclosure through which an optical train travels. In an embodiment, the temperature within the optical enclosure is maintained within 500 m° C. of a target temperature.

In an embodiment, at least one of the heat pumps is a Peltier thermoelectric heating/cooling device. In another embodiment, all of the heat pumps are Peltier devices. Any heat pump can be used to maintain the temperature of the optical enclosure and/or the chip as would be obvious to one skilled in the art. The heat pumps can also be coupled to a heat sink and/or a fan to provide for more efficient cooling of the heat pump.

A heat pump for heating a microfluidic chip can be part of a thermal subsystem of the temperature control unit. In an embodiment, the thermal subsystem comprises a heat sink and support apparatus for holding the chip into thermal contact with a heat pump. The thermal subsystem or part of the thermal subsystem (for example, the support apparatus) can be contained within an optical enclosure of a device of the invention to thermally separate the chip from the rest of the device. The support apparatus of the thermal subsystem may also have holes adapted and configured to receive a pipette tip or other device for delivering fluid to a microfluidic chip of the invention.

Figure 11:
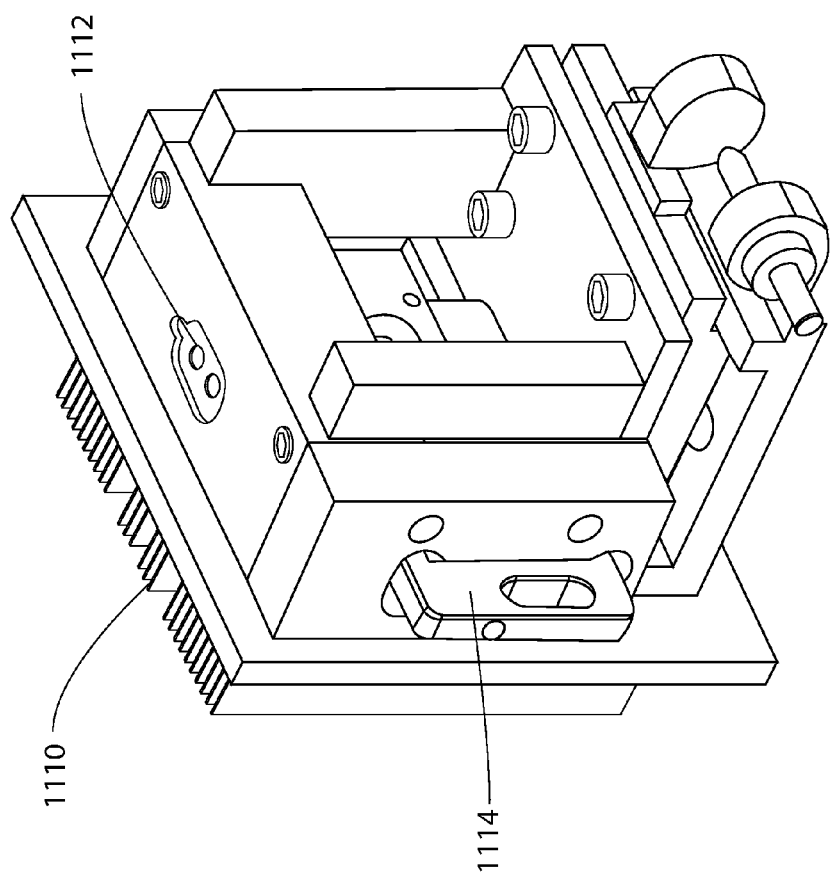
FIG. 11 shows the interior components of an interferometric device comprising a heat pump (1110), a sample delivery aperture (1112), and a microfluidic chip cartridge (1114).

FIG. 11 demonstrates a thermal subsystem of a device of the invention for maintaining the temperature of a microfluidic chip within 5 m° C. of a target temperature, wherein the subsystem comprises a heat pump (1110), a sample delivery aperture (1112), and a microfluidic chip cartridge (1114). The chip holder or cartridge (1114) is inserted through an aperture in the side of the subsystem in order to put the chip into thermal contact with the heat pump (1110). In this embodiment, the heat pump (1110) is a Peltier device coupled to a heat sink for rapid and accurate control of the temperature of the chip. The thermal subsystem also comprises a sample delivery aperture (1112) to deliver a sample to the chip after it has been placed in thermal contact with the heat pump (1110).

The chip can be formed of any suitable optically transmissive material, such as plastic (for example, polymeric material), glass, or quartz. In an embodiment, the material from which the chip is manufactured must have a different index of refraction than that of a sample volume to be tested. The chip can be mounted on or brought into thermal contact with the thermal subsystem of the temperature control unit. The chip and/or the thermal subsystem can be affixed to a translation stage that allows adjustment of the chip relative to the laser beam. For example, the chip can be tilted slightly (for example, approximately 7°) so that the backscattered light from the sensing area of the chip can be directed onto the photodetector. The thermal subsystem can maintain the sample in the sensing area within 5 m° C. of a target temperature. In an embodiment, the refractive index of a sample varies linearly with its temperature. Alternatively, this characteristic also allows the detection device to be utilized for making temperature measurements.

In another embodiment, at least one fan is used to move heat away from the device. A fan can move heat away from the electronics compartment or the optical compartment. The fans can be randomly or continuously operated or can be part of the temperature control unit.

Circuitry of the temperature control unit can be a circuit board, such as a computer board or a PC board, or can be a series of wires for connecting different parts of the thermal control unit, such as the temperature sensors, heat pumps, and a computer. A computer system can be used to receive temperatures from temperature sensors of the temperature control unit of the device and to operate and control heat pumps of the device to maintain the key target temperatures. In an embodiment, the computer system uses temperature feedback from the temperature sensors as the basis for control of a heat pump.

A device of the invention may also comprise an instrument control unit. The instrument control unit can comprise circuitry, a computer system and devices for controlling instruments (for example, a photodetector and a coherent light source).

Figure 4:
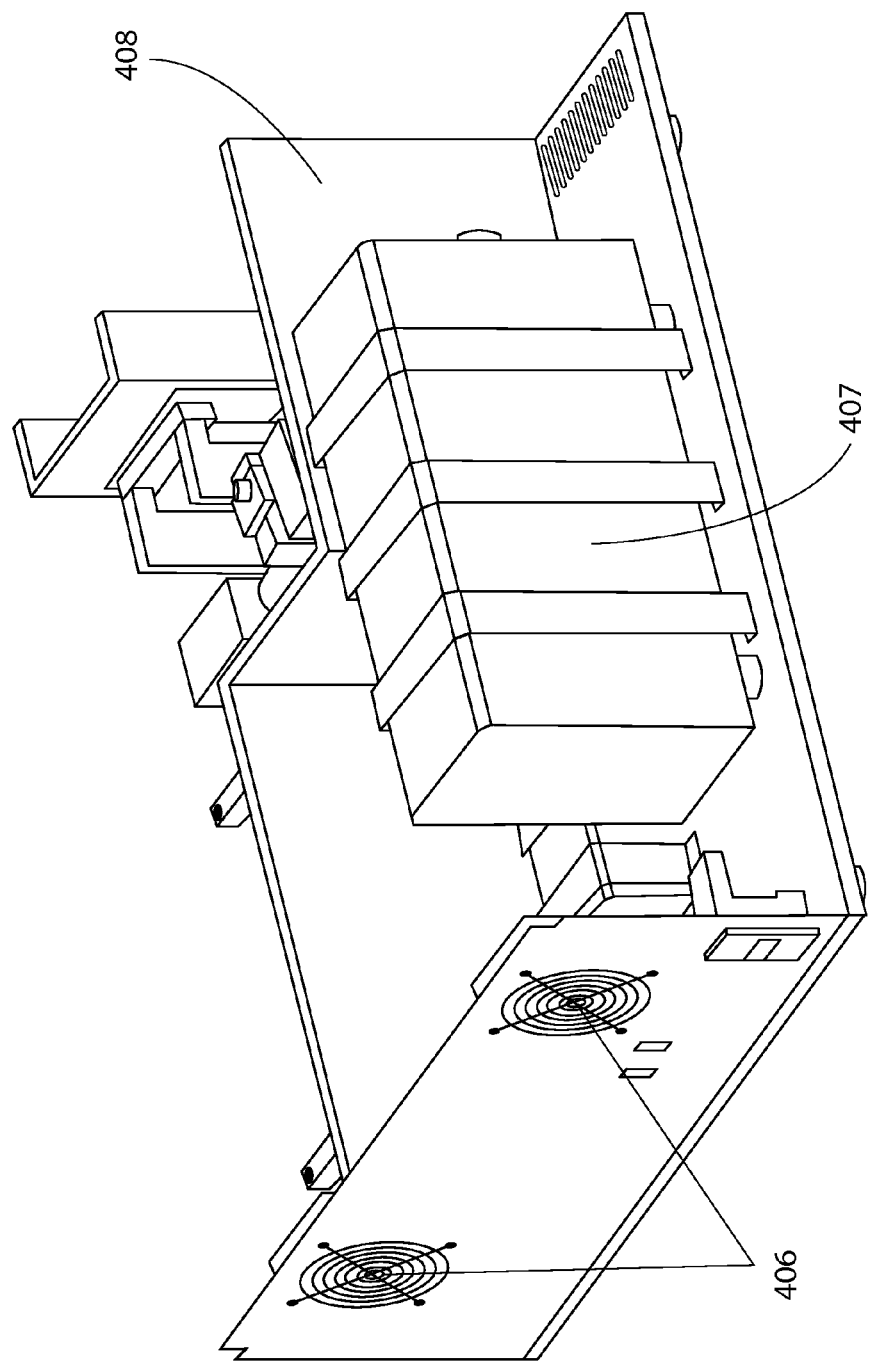
FIG. 4 shows the interior components of an interferometric device comprising of an interferometric detection device comprising at least two fans (406), electronics circuitry (407) and a thermal separator (408) that separates heat-generating circuits from the optical assembly.

FIG. 4 illustrates the interior components of an exemplary interferometer comprising at least two fans (406), an electronics assembly (407) and a thermal separator (408). The electronics assembly (407) is located within the electronics compartment of the device which is thermally separated from an optical compartment and/or optical bench by a thermal dam (408). The thermal separator (408), also referred to herein as a thermal dam (408), can be a thermal insulator (408). The electronics assembly (407) can comprise at least one of the circuitry for the temperature control unit and the circuitry from the instrument control unit. In the exemplary device in FIG. 4, two fans (406) are used to ventilate the device in order to maintain the temperature within the device at the desired levels. The fans (406) can be connected to the temperature control unit in order to maintain the temperature of the chip within 5 m° C. of a target temperature or to maintain the temperature of the medium through which the optical train travels within 500 m° C. of a target temperature.

In an aspect of the invention, an interferometric detection device comprises: a) an optical assembly comprising: i) a microfluidic chip with at least one microfluidic channel with a sensing area; ii) a coherent light source positioned to direct a beam toward the microfluidic channel wherein the path of the beam defines an optical train and generates a back-scatter light pattern; and iii) a photodetector configured to detect the back-scatter light pattern; and b) an electronics assembly comprising circuitry for a temperature control unit configured to control the temperature of a medium through which the optical train travels and the temperature of the microfluidic chip; wherein said optical train and chip are thermally separated from said photodetector and said optical assembly is thermally separated from said electronics assembly. The temperature within the optical assembly can be monitored by a temperature sensor. The optical assembly may further comprise an optical enclosure wherein the temperature within the enclosure can be controlled by at least one heat pump or a temperature control unit of the invention.

In an embodiment, the electronics assembly further comprises circuitry for an instrument control unit, wherein the instrument control unit communicates with at least one of the coherent light source and the photodetector.

Figure 5:
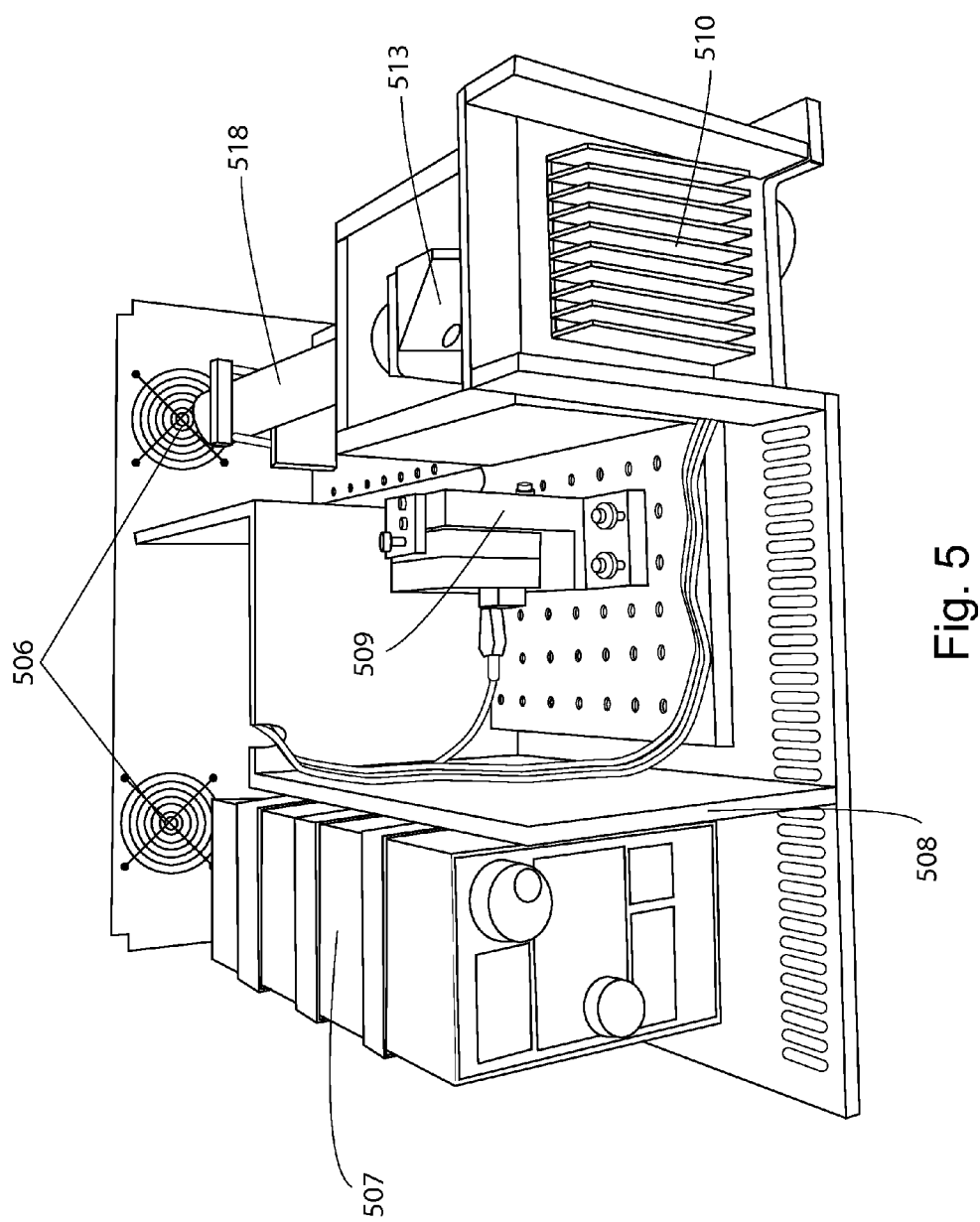
FIG. 5 shows the interior components of an interferometric device comprising of an interferometric detection device comprising at least two fans (506), an electronics assembly (507), a thermal separator (508), a coherent light source (518), optical unit (513) that can include a beam splitter and a mirror to direct light to the photodetector, a heat pump (510) that controls heat in chip and a photodetector (509).

FIG. 5 shows the interior components of an interferometric device comprising of an interferometric detection device comprising at least two fans (506), an electronics assembly (507), a thermal separator (508), a photodetector (509), a heat pump (510), and a coherent light source (518). The photodetector (509), coherent light source (518), and heat pump (510) are attached to an optical bench, such that small movements of the device will not affect measurements and detection by the device. A series of wires travel through a notch in the thermal separator (508) to connect the electronic components (507) in the electronic compartment, such as the circuitry of the temperature control and instrument control units, to components in the optical compartment on the optical bench. Fans (506) are also provided to ventilate the device. Also shown in FIG. 5 is an aperture in the optical enclosure (shown without a lid) to provide the back-scattering light pattern to the photodetector. The heat pump (510) also comprises a heat sink as shown in the figure.

Interferometric detection of an analyte in a sample using a device of the invention is capable of measuring the concentration of an analyte in a sample at low concentrations (for example, pM or fM concentrations). Also, a device of the invention can have a sensing area with a volume of no more than 100 nl. In an embodiment, the volume of the sensing area is less than 10 nl. In another embodiment the volume of the sensing area is 1 nl. In another embodiment, the volume of the sensing area is less than nl.

In an embodiment, a device further comprises an optical enclosure that thermally separates the optical train from the photodetector, wherein the enclosure comprises means to allow the back-scattering light pattern to reach the photodetector. The means can be any optics used to direct or receive light, such as a mirror, a dichroic mirror, fiberoptics, or any other means as would be obvious to one skilled in the art.

In an aspect, the invention discloses an interferometric detection device comprising an optical enclosure containing a microfluidic chip with a sensing area and a medium through which an optical train travels to the sensing area, wherein the temperature of the medium is maintained within 500 m° C. of a target temperature by a computer-controlled thermal regulation system. The computer-controlled thermal regulation system can be any active or passive temperature regulation system. In an embodiment, the computer receives temperature feedback data, for example, from a temperature sensor such as a thermocouple. The computer can comprise a processor to process the temperature data from the sensor or a plurality of sensors. The processor can also provide instructions and/or a process for controlling a heat pump to maintain the temperature of the sensing area of the microfluidic chip and/or the optical enclosure.

In another aspect, this invention provides a microfluidic system that can deliver between 10 microliters and 0.1 microliter of a liter of a sample to a sensing area without substantial loss of analyte during the delivery. The system maintains short distances between sample introduction via micropipette and the sensing area and small volumes.

In an aspect of the invention, a microfluidic chip is provided comprising at least one channel, wherein part of the channel is a sensing area for interferometric measurement of an analyte in a fluid sample in the sensing area. The microfluidic channels of the devices of this invention generally have a cross-sectional area of no more than 0.003 mm$^2$, or no more than 0.3 mm$^2$. The fluidic channel can comprise an adapter channel that couples to an adapter that is configured to receive a pipette tip from a user. The adapter channel leads to a sensing area, from which an outlet channel can allow a sample to exit the chip. In an embodiment, the sensing area of the chip has a volume of less than 500 nl. In another embodiment the volume of the sensing area is less than 100 nl. In another embodiment, the volume of the sensing area is less than 10 nl. In a further embodiment, the volume of the sensing area is 1 nl. The sensing area is configured to measure the concentration of an analyte in a fluid sample. In an embodiment, the concentration of the analyte in the sample is less than 100 nM, less than 10 nM, less than 1 nM, less than 100 pM, less than 10 pM or less than 1 pM. The concentration of the analyte in the sample can be in the fM concentration range (at least 100 fM or at least 10 fM).

Microfluidic Chip

In another aspect, the invention provides a microfluidic system comprising: a) a microfluidic chip comprising a microfluidic channel opening onto a chip inlet and a chip outlet, wherein the channel comprises: (i) a sensing area having a volume between about 0.1 nl and about 10 nl; and (ii) a fluid delivery area adapted to deliver fluid to the sensing area; and b) a fluidic adaptor comprising a fluidic adaptor channel opening onto an adaptor inlet and an adaptor outlet, wherein the adaptor inlet is adapted to mate with a pipette tip adapted to deliver between 0.1 microliter and 10 microliters of fluid and the outlet is mated with the chip inlet, wherein said adaptor channel and the fluid delivery area have a volume of no more than 1 microliter and a length of no more than 7 mm.

In another aspect of the invention, a microfluidic device can receive between 0.1 and 10 microliters of a sample having an analyte at a picomolar concentration, and deliver at least a portion of the sample through a microfluidic channel to a sensing area with a change in analyte concentration of no more than 5%.

In certain microfluidic systems, analyte can become bound to the walls of fluidic channels or become lost in other ways, resulting in a sample in the sensing area having a measurably different concentration, when compared to its original concentration. This is particularly true when small sample volumes are delivered over long distances in conditions in which the surface area:volume ratio of the system is high. Accordingly, the dimensions of the adaptor and adaptor channel can be selected to diminish toss of analyte. For example, the system can be configured so that when 1 microliter of a solution of 10 picomolar bovine serum albumin in phosphate buffered saline is delivered from a micropipette tip through the adaptor and adaptor channel to the sensing area, the loss if BSA concentration is no more than 5%, 1% 0.05% or 0.01%. This is the case, for example, when the adaptor channel and the fluid delivery area have a volume of no more than 1 microliter and a length of no more than 7 mm. Also, the dimensions and delivery volume are not so small that at a standard laboratory micropipette cannot deliver 1 microliter of sample because the back pressure of the system is greater than the pressure delivered by the micropipette. A standard device for measure in this regard is the Gilson Pipetman P2 (Part F144801). (Gilson, Inc. Middleton, Wis., USA.)

Figure 12:
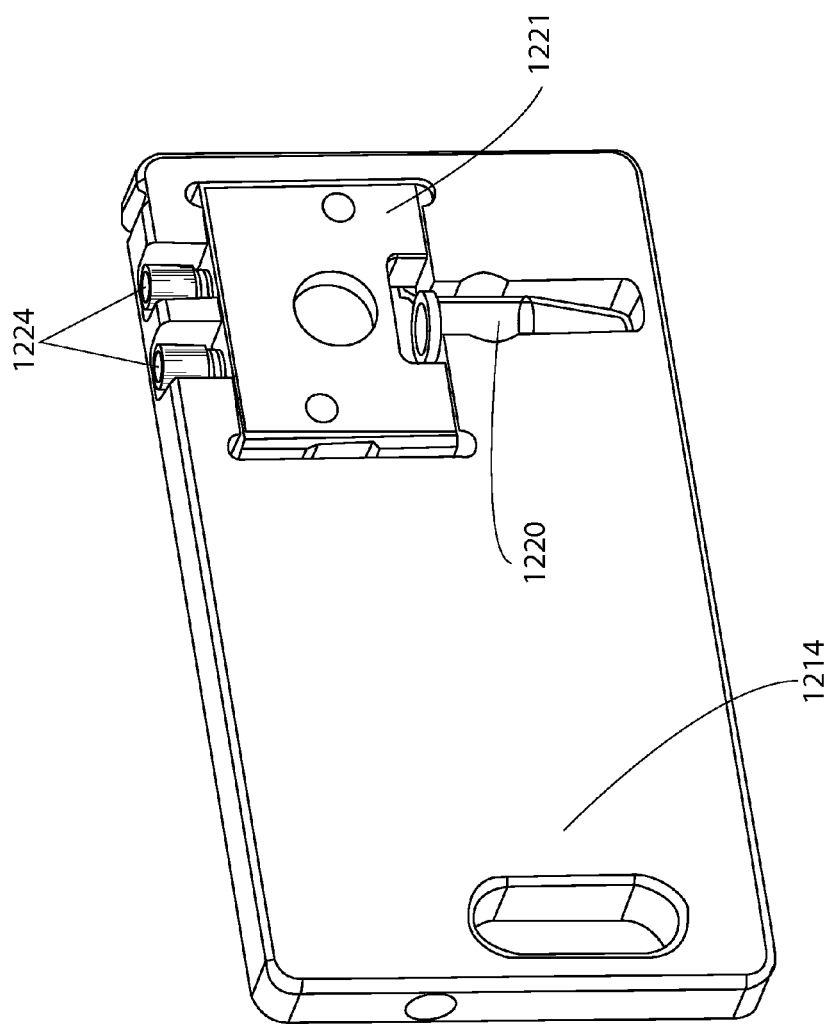
FIG. 12 shows a microfluidic chip cartridge (1214) comprising a waste receptacle (1220), a microfluidic chip holder (1221), and at least two sample ports (1224).
Figure 13:
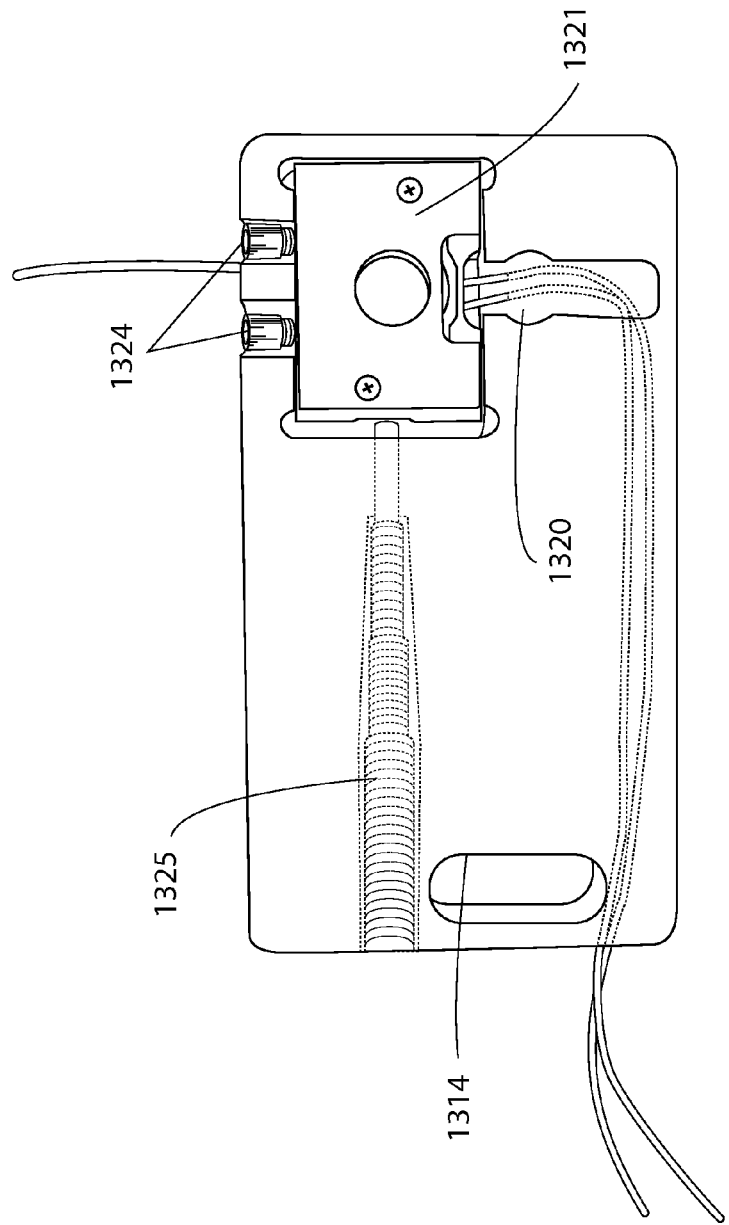
FIG. 13 shows another microfluidic chip cartridge (1314) comprising a waste port (1320), a microfluidic chip holder (1321), at least two sample ports (1324), and a microfluidic chip holder retention mechanism (1325).

A microfluidic chip of the invention can be adapted and configured to fit snugly within a chip holder. In an embodiment, the chip holder is designed to firmly hold the chip in place in one dimension and allow the chip to rotate about an axis perpendicular to the sensing area. The chip holder can comprise a spring and/or a screw for snugly holding the chip in place within the holder. An exemplary chip holder or cartridge of the invention is demonstrated in FIG. 12. FIG. 12 shows a microfluidic chip cartridge (1214) comprising a waste receptacle (1220), a microfluidic chip positioner (1221), and at least two sample ports (1224). The sample ports (1224) are configured to fit an adapter and adapter channel that are configured to mate with a pipette tip for sample delivery to the chip. The chip can be held in place by a positioner (1221), such as a metal plate with tightening screws. The chip can be manually inserted into the chip holder or cartridge (1214). In an embodiment, the chip is disposable while the chip holder (1214) can be used for numerous different chips with a device of the invention. FIG. 12 also demonstrates a waste receptacle (1220) that can be incorporated into the chip cartridge (1214) to receive waste sample after it has passed through the microfluidic chip. The waste receptacle (1220) can be a disposable vial. FIG. 13 shows another microfluidic chip cartridge (1314) comprising a waste port (1320), a microfluidic chip holder (1321), at least two sample ports (1324), and a microfluidic chip holder retention mechanism (1325). The microfluidic chip holder retention mechanism (1325) can be used to firmly hold the chip in the holder (1321) along the axis of the mechanism (1325). In an embodiment, the chip can rotate within the holder (1321) along an axis perpendicular to the retention mechanism (1325).

Figure 14:
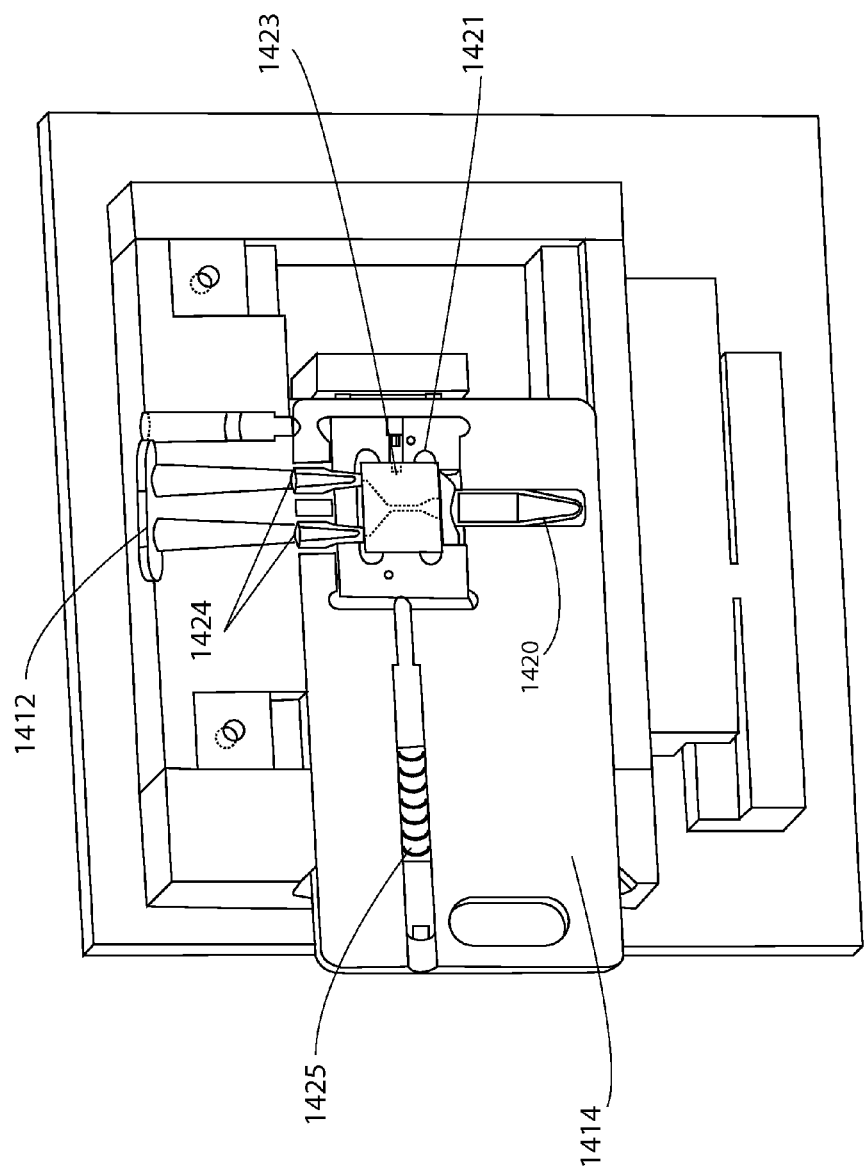
FIG. 14 shows the interior components of an interferometric device comprising an opening for access to a microfluidic chip cartridge (1412) and a microfluidic chip cartridge (1414) comprising a waste receptacle (1420), a microfluidic chip holder (1421), a microfluidic chip (1423), at least two sample ports (1424), and a microfluidic chip holder retention mechanism (1425).

FIG. 14 shows the chip holder in position to put the chip into thermal contact with a heat pump. FIG. 14 demonstrates an interferometric device comprising an opening for access to a microfluidic chip cartridge (1412) and a microfluidic chip cartridge (1414) comprising a waste receptacle (1420), a microfluidic chip holder (1421), a microfluidic chip (1423), at least two sample ports (1424), and a microfluidic chip holder retention mechanism (1425).

The microfluidic chip can be made of a material that has a different (e.g., higher) refractive index than the sample inside. The chip can be formed of any suitable optically transmissive material, such as glass, quartz, borosilicate, silica (e.g., fused silica) or a polymeric material, e.g., a plastic such as polyacrylate, cyclic olefin copolymer, polydimethyl siloxane, polycarbonate, and polymethyl methacrylate.

The microfluidic chip can have an internal compartment that can hold the sample. Typically, the compartment will take the shape of a bore. The bore may be have a curved cross section that is, for example, circular, substantially circular, hemicircular or elliptical. Backscatter fringe patterns are easily produced with when the substrate includes a compartment having curved or angular walls through which the light passes to reach the sample. However, useful backscatter patterns also have been produced with rectangular shaped compartments.

In an embodiment, the microfluidic chip comprises two layers. In one layer, the chip is etched with at least one channel. The other layer can be adhered to the etched layer to form a fluidic channel within the chip. In an embodiment, both layers of the chip are etched and aligned. In another embodiment, the channels of the microfluidic chip are semi-circular. In another embodiment, the channels of the chip are rectangular or square. In another embodiment, the channels of the chip are cylindrical. The channels of the chip can be of any shape as can be etched into a layer. The layers of the microfluidic chip are made of polymers in a preferable embodiment. The polymers are clear, such that a light can pass through the microfluidic chip. The chip can be constructed of a variety of materials including, but not limited to, glass, silica, PDMS, and PMMA. If a microfluidic chip is inserted into thermal contact with a heat pump of a device of the invention, the heat pump can comprise a light absorbing surface, such that after light has traveled through the clear chip, no light is reflected from the heat pump. However, if a sample is in the sensing area of a microfluidic chip, light may be back-scattered from the sample and read with a photodetector. The back-scattering to the light from the sample can be used to measure the concentration of an analyte in the sample.

In an embodiment, the sensing area has a generally semi-circular cross-sectional shape, which can provide a unique multi-pass optical configuration based upon the interaction of the coherent light and the curved surface of the channel. The shape can allow interferometric measurements in small volumes at high sensitivity. In another embodiment, the adapter channel and sensing area together comprise a capillary tube. The chip can comprise two channels wherein the second channel can be used as a measurement sensing area or a reference sensing area.

Figure 15B:
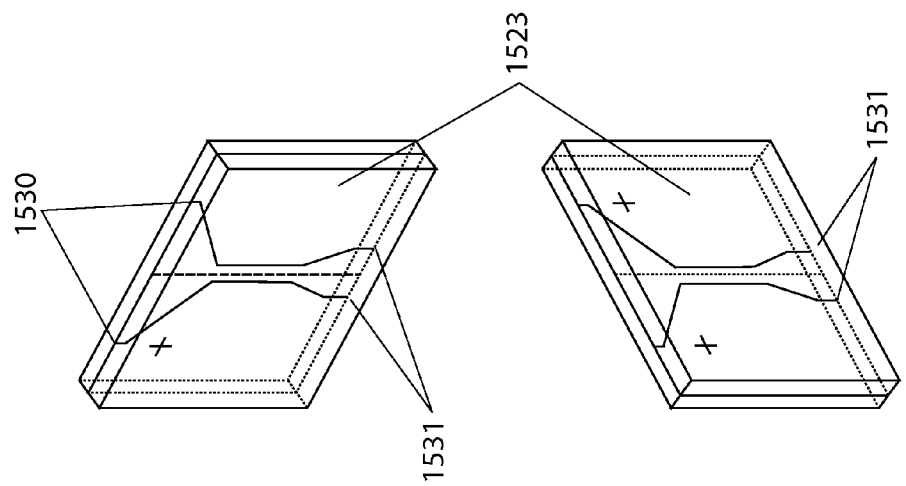
FIG. 15B shows a microfluidic chip (1523) comprising at least two microfluidic channels each comprising an entrance port (1530) and an exit port (1531).
Figure 15A:
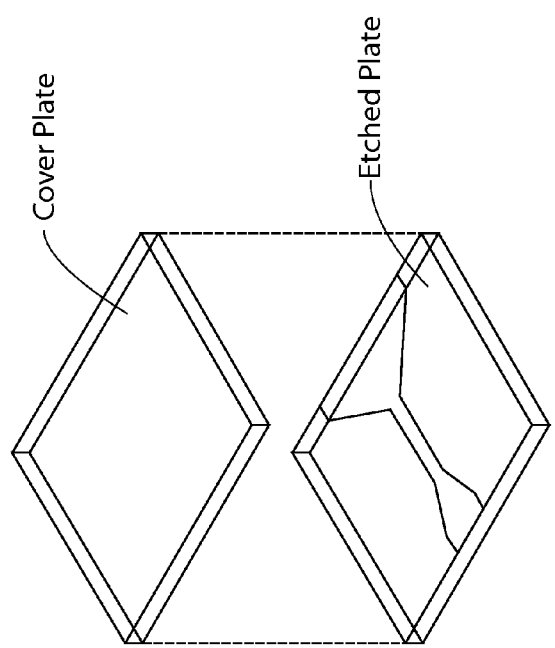
FIG. 15A shows a microfluidic chip comprising a cover plate bonded to an etched plate.
Figure 16:
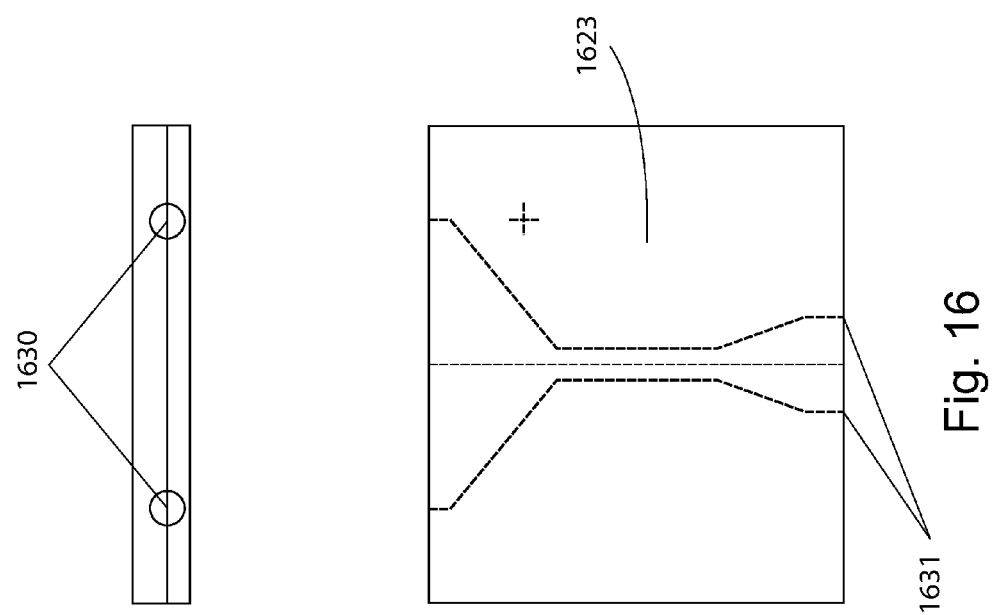
FIG. 16 shows a microfluidic chip (1623) comprising at least two microfluidic channels each comprising an entrance port (1630) and an exit port (1631).
Figure 17:
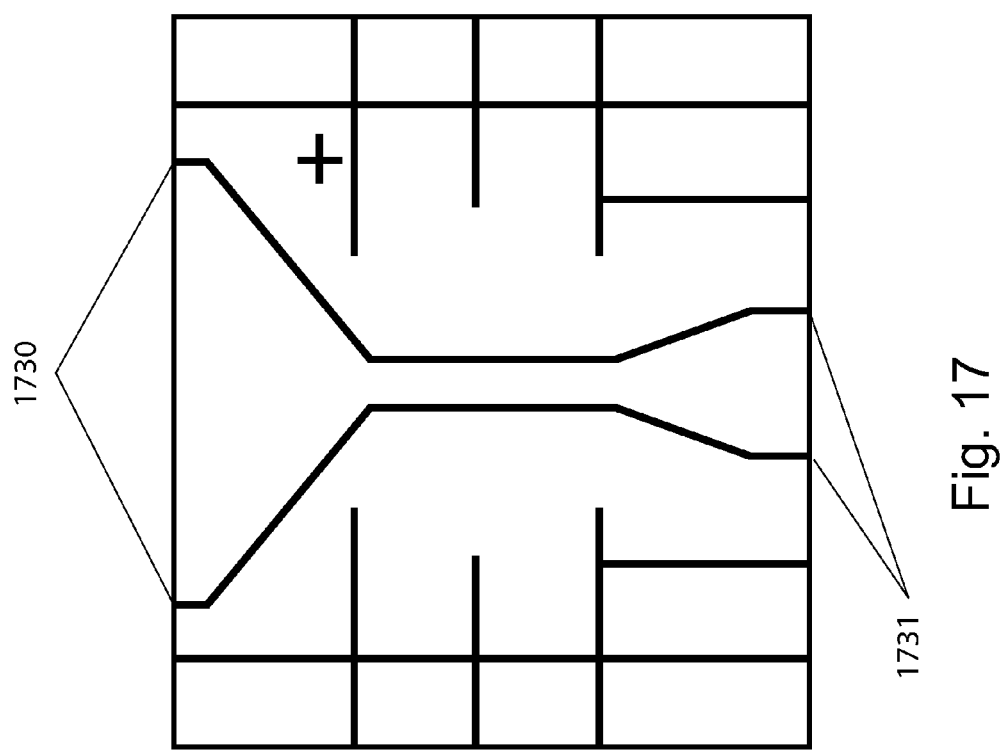
FIG. 17 demonstrates a microfluidic chip with two entrance ports (1730) and two exit ports (1731).

FIG. 15A shows a microfluidic chip comprising a cover plate bonded to an etched plate to form an adapter channel and sensing area within the chip. FIG. 15B shows a microfluidic chip (1523) comprising at least two microfluidic channels each comprising an entrance port (1530) and an exit port (1531). FIG. 16 shows a microfluidic chip (1623) comprising at least two microfluidic channels each comprising an entrance port (1630) and an exit port (1631). FIG. 17 demonstrates a microfluidic chip with two entrance ports (1730) and two exit ports (1731).

In one embodiment the chip may comprise fluid channels that are symmetrical on the center line. In another embodiment the exit ports are located on an edge of the chip. The exit ports may be treated with a hydrophobic solution, such as a Teflon based solution. In another embodiment the surface area at the entry port locations is adequate for sealing with a low pressure fitting.

In an aspect, the invention provides an adapter configured to couple a microfluidic chip of the invention with a pipette tip. The adapter is configured to receive a pipette tip and deliver a sample from the pipette to a channel of the chip. The sample can then move through the channel to the sensing area. Based on the dimensions of the channel and sensing area in the microfluidic chip, only a small sample is needed to obtain enough sample in the sensing area. As a sample moves through a channel, the sample can adhere to the walls of the channel, making it difficult to measure small sample volumes of analytes of very dilute concentrations. However, by using relatively short channels (for example, a few millimeters in length) and low volume channels, a small sample volume of very dilute concentration can be measured using a chip, adapter and device of the invention. Also, the sensing area of the chip can be on the order of about 1 to 10 nl, which requires less sample to travel through the fluidic channels of the chip to reach the sensing area. In an embodiment, less than 10 microliters of sample is inserted into a chip or device of the invention. In another embodiment, less than 1 microliter of sample is inserted into a chip or device of the invention.

It can be advantageous to measure the analyte concentration from a very small volume of sample. For example, the smaller the volume of sample needed to run a test, the more tests that can be executed on a single sample taken from a user. In addition, it may shorten and limit the time needed to obtain a sample from a user.

Methods

A device of the invention can be used for any application that requires interferometric measurements; however, it is particularly applicable for quantifying an analyte in a sample or solute in a solution. In one embodiment, the fluid sample is a liquid, which can be a substantially pure liquid, a solution, or a mixture (e.g., biological fluids, cellular fluids). In a further aspect, the fluid can further comprise one or more analytes.

A device of the invention can be used to for the creation of molecular interaction products that deliver free-solution or surface-bound, label-free kinetic, and quantitative end-point biochemical- and cell-based assays. The methods and devices of the invention may also have implications in the emerging field of personalized medicine, beginning with research applications involving biomarker discovery and assay development in academic, government, and industrial laboratories. Devices of the invention may also be used for benchtop research use, and may be adapted to devices and assays for hand-held, point-of-care clinical diagnostics and point-of-analysis biodefense applications.

A device of the invention can be scalable, with possible system configurations ranging from miniaturized appliance-scale and hand-held devices to automated, high throughput, multiplexed systems. A device of the invention as disclosed herein may be used as a benchtop research product that can measure both free-solution and surface-bound molecular interaction kinetic and quantitative end-point assays targeted for assay development in basic research, pharmaceutical, clinical diagnostic, and biodefense applications.

Currently being validated for a variety of cell-based assays, BSI devices may be particularly valuable where trace sample requirements, extraordinary sensitivity, and/or free-solution analysis are required. Unlike other biosensor techniques, BSI does not require significant knowledge of the interacting species and eliminates the need for finessing surface attachment chemistries.

A device and method of the invention can be used for end-point assays and dissociation constant measurements. Molecular interactions that can be examined include biomolecules such as DNA, RNA, proteins, carbohydrates, small drug molecules, and lipids, along with bacteria, viruses, cells and cell lysates. Experiments can be conducted in free-solution which often only requires minimal sample, device, or measurement preparation before the experiment.

A device of the invention can be utilized for methods of detection of an analyte in a free-solution sample. In contrast to conventional techniques that observe immobilized analytes, free-solution analysis techniques mimic in vivo measurements, because analytes enjoy unrestricted freedom in all three dimensions during measurement.

In an embodiment, methods and devices of the invention relate to a method for free-solution determination of molecular interactions comprising the steps of providing a microfluidic chip having a sensing area formed therein for reception of a fluid sample to be analyzed. The microfluidic chip can be in contact with an adapter configured to receive a pipette tip, wherein a user can pipette a sample in the chip for analysis. A coherent light beam is directed onto the chip such that the light beam is incident on the sensing area to generate backscattered light through reflective and refractive interaction of the light beam with the sample, the backscattered light comprising interference fringe patterns including a plurality of spaced light bands whose positions shift in response to changes in the refractive index of the fluid sample; detecting positional shifts in the light bands. The formation of the one or more interaction products of a first analyte with a second analyte can also be detected from the positional shifts of the light bands in the interference patterns.

The disclosed techniques can determine the interaction between one or more analytes by monitoring, measuring, and/or detecting the formation and/or steady state relative abundance of one or more analyte interaction products from the interaction of the one or more analytes. The determination can be performed qualitatively or quantitatively. Interaction rate information can be derived from various measurements of the interaction.

The photodetector can be a camera, such as a CCD camera, that collects images. The images can be projected on a monitor for visual analysis. For example, the monitor can be calibrated and/or the operator can visually detect changes in the fringe pattern over time. Alternatively, the image can be subjected to a variety of mathematical algorithms to analyze the fringe pattern, e.g., by a computer system. One example of an algorithm used to analyze fringe pattern is a fast Fourier transform cross-correlation to quantitate a positional shift of a fringe. Other cross-correlation methods and fringe shift algorithms may be used.

The data processing systems of the invention can be adapted to perform an analysis which comprises one or both of: (a) the determination of the angle with respect to the light path at which there is an abrupt change in the intensity of the lighter fringes, or (b) the determination of the position of fringes of a low frequency component of the variation of intensity between the lighter and darker fringes. In a further aspect, the data processing systems further comprise a processor programmed to determine a characteristic property of the fluid sample in the channel by performing a method comprising the steps of: computing an overlapping product of a signal A and a signal B from the detector, and assigning values to elements of a list based on the overlapping product; summing a set of elements of the list to produce a value q; multiplying a set of elements of the list by an odd function; summing one or more products from the multiplying step to produce a value p; and calculating the shift between signal A and signal B as a function of p divided by q.

The data analysis system can be a processor, such as a PC, or any other system capable of calculating measurements. The system can be a part of an instrument control unit of the invention or connected to an instrument control unit. The data analysis system can be electronically connected to a board or circuitry of a device of the invention for control of the instruments, such as the photodetector or coherent light source.

In a yet further aspect, the analysis comprises one or both of: (a) the observation of the angle with respect to the light path at which there is an abrupt change in the intensity of the lighter fringes, or (b) the observation of the position of these fringes of a low frequency component of the variation of intensity between the lighter and darker fringes. In a still further aspect, at least one the interface involving the sample at which light is reflected is curved in a plane containing the light path, the curved interface being convex in the direction facing the incoming light if it is the interface between the first material and the sample and being concave in the direction facing the incoming light if it is the interface between the sample and the further material.

Back-scattering interferometry can measure free solution measurements. One example of a free solution measurement in life science applications can be when a device of the invention is used to detect the binding of two biological macromolecules in a sample or samples by examining a change in the interference pattern produced from the reflection and refraction of the sample(s) upon mixing the two biological macromolecules. In contrast, many conventional methods require measuring the amount of a molecule bound with monoclonal antibody to a solid support, and then binding a secondary antibody that has a label attached to it for visualization. In contrast, a method and device of the invention method does not require that the molecule being examined be bound to a solid support, as the measurement could be made in free solution.

Other surface-bound biosensor techniques can be supplanted by the disclosed free-solution methods and systems. For example, the objective of surface plasmon resonance (SPR), optical wave-guide techniques, grating coupled optical waveguide techniques, microcantilever techniques, atomic force microscopy, acoustic techniques, as well as labeled techniques (including chemiluminescence, ELISA, fluorescence detection, and solid or liquid scintillation) can be achieved with the disclosed systems and methods.

In some instances, a method for determining a refractive index of a liquid comprises: providing a liquid to the sensing area of a device as described herein and detecting movement of a fringe pattern generated by interferometric analysis with the device to indicate a change in the refractive index of the liquid. The liquid can comprise a first and second biochemical species. Using the methods as described herein, the interaction of the first and second biochemical species can be monitored by detecting a change in the refractive index of the liquid over time as determined by interferometry utilizing a device described herein. In some embodiments, a change in refractive index can indicate a change in temperature. However, by utilizing a device herein, temperature of the liquid can be held stable, therefore allowing for more accurate measurement of other happenings, such as biochemical species interaction or ligand binding in the liquid. In an embodiment, the first and second biochemical species are selected from the group comprising: complimentary strands of DNA, complimentary proteins and antibody-antigen pairs. In another embodiment, the liquid comprises a ligand and one or more receptors. A method herein can be used to determine whether the ligand binds with the one or more receptors by monitoring changes in the refractive index of the liquid. In yet another embodiment, a method herein can be used to analyze a label-free hybridization reaction in the liquid.

In a further embodiment, the invention relates to a method for real-time, free-solution determination of molecular interactions comprising the step of detecting the formation of one or more interaction products of two unlabeled, non-immobilized analytes, wherein at least one of the analytes is present during the determination at a concentration of less than about $5.0 \times 10^{-5}$M.

In an embodiment, the invention can relate to a method for real-time, free-solution determination of molecular interactions comprising the step of detecting the formation of one or more interaction products of two unlabeled, non-immobilized analytes, wherein at least one of the analytes is present during the determination in a solution with a volume in the sensing area of less than about 10 nl.

The invention can relate to a method for free-solution determination of molecular interactions comprising the steps of providing a chip having a channel formed therein for reception of a fluid sample to be analyzed; introducing a first sample comprising a first analyte to be analyzed into the channel; establishing a baseline interferometric response by directing a coherent light beam onto the chip such that the light beam is incident on the sensing area to generate back-scattered light through reflective and refractive interaction of the light beam with the sample. The backscattered light can comprise interference fringe patterns including a plurality of spaced light bands whose positions shift in response to changes in the refractive index of the first sample. A second sample comprising a mixture of the first analyte can be introduced to the same channel or a second channel and a second analyte to be analyzed. The baseline of the first measurement can be used to quantitate the second analyte in the second sample.

Figure 18:
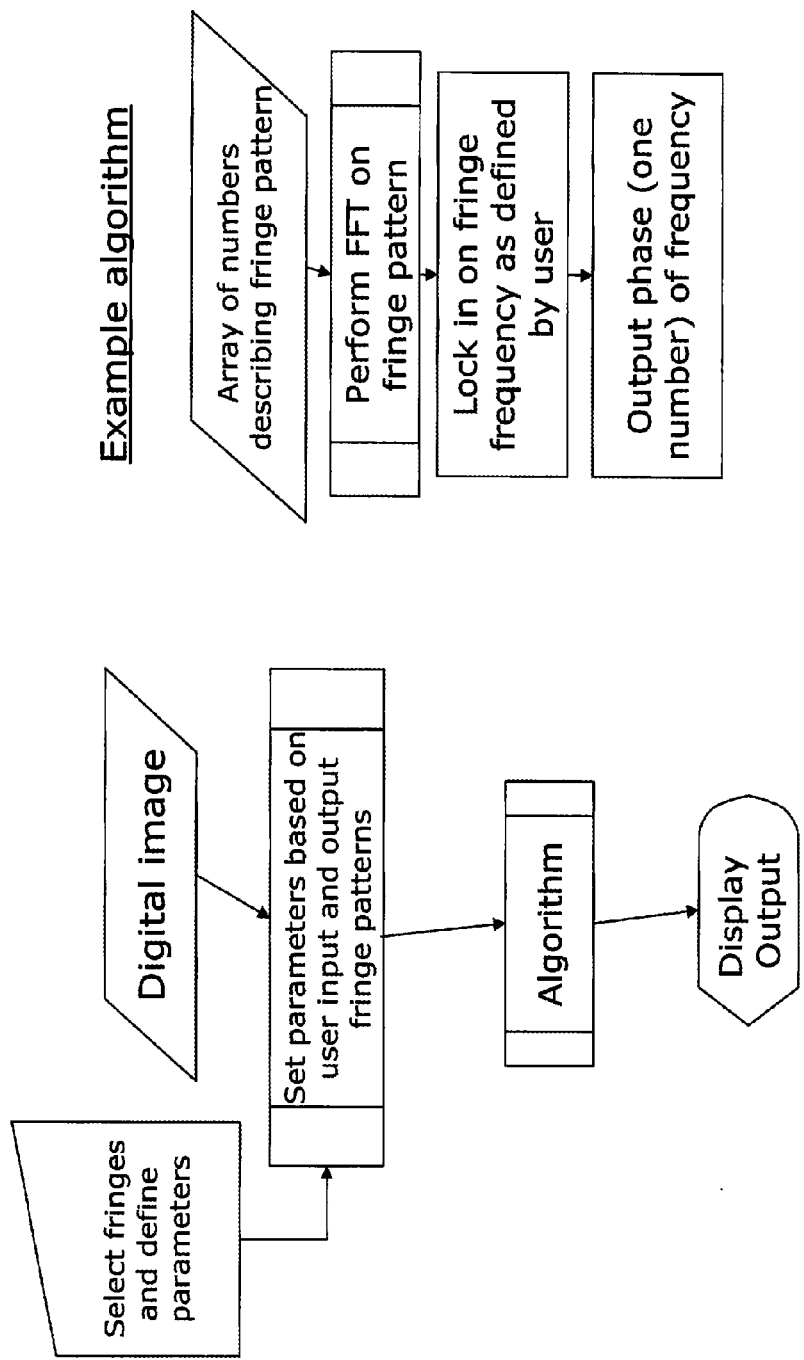
FIG. 18 illustrates an exemplary embodiment of analyzing an interference pattern or fringe achieved from interferometric measurements of a sample liquid.

FIG. 18 illustrates an exemplary embodiment of analyzing an interference pattern or fringe achieved from interferometric measurements of a sample liquid. A fringe pattern or multiple fringe patterns are selected and parameters can be defined describing those patterns. A digital image of the interference and the parameters can be used to obtain an array or matrix of numbers describing a fringe pattern. A fast Fourier transform can be used to convert the array to the frequency domain and a fringe frequency can be defined by a user. Using this method and/or cross-correlation of a fringe pattern observed at discrete times, the phase of the frequency can be output and displayed. This method and process can be performed on a computer system, either with a set of instructions to perform the calculations, or a computer system with firmware designed to perform a method. The computer system can also comprise a user interface when needed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An interferometric detection device comprising:
   (a) a microfluidic chip with a sensing area,
   (b) a coherent light source positioned to direct a beam along an optical train toward said sensing area to generate a back-scattering light pattern;
   (c) a photodetector configured to detect the back-scattering light pattern; and
   (d) an optical enclosure containing a medium through which said optical train travels to the chip;
   wherein the device is configured to maintain a temperature of said sensing area within 20 m° C. of a first target temperature and to maintain a temperature of the medium within 500 m° C. of a second target temperature under conditions in which ambient temperature changes from 0.1° C. to 5° C. over 5 minutes.

2. The device of claim 1, further comprising an optical bench, wherein said microfluidic chip, said optical enclosure, said coherent light source, and said photodetector are attached to said optical bench, and wherein said optical bench provides vibrational damping.

3. The device of claim 2 further comprising an electronics compartment comprising circuitry for a temperature control unit; and circuitry for an instrument control unit, wherein the instrument control unit communicates with at least one of the coherent light source and the photodetector.

4. The device of claim 3 further comprising a dam that thermally separates the optical bench from said electronics compartment.

5. The device of claim 4, wherein said temperature control unit comprises:
   a) a plurality of temperature sensors that measure at least one of:
      1) the temperature at a surface of the chip,
      2) the temperature within the optical enclosure,
      3) the temperature within the optical assembly,
      4) the ambient temperature, and
      5) the temperature within the electronics assembly;
   b) a first heat pump configured to transfer heat to or from said medium inside the optical enclosure;
   c) a second heat pump configured to transfer heat to or from a surface of the chip; and
   d) circuitry comprising an electrical connection configured to regulate temperature at the chip surface and of the medium inside the optical enclosure by receiving measurements from the temperature sensors and to regulating heat flow in the heat pumps as a function of the measurements.

6. The device of claim 5, wherein said first heat pump and said second heat pump are Peltier devices.

7. The device of claim 1 wherein the first and second target temperatures are between 15° C. and 37° C.

8. The device of claim 1 wherein the coherent light source is selected from a He/Ne laser, a VCSEL laser and a diode laser.

9. The device of claim 1 wherein the photodetector comprises a CCD or CMOS camera.

10. The device of claim 1 configured to maintain a temperature of said medium within 100 m° C. of said second target temperature.

11. An interferometric detection device comprising:
    a) an optical assembly comprising:
       i) a microfluidic chip with at least one microfluidic channel with a sensing area;

ii) a coherent light source positioned to direct a beam toward the microfluidic channel wherein the path of the beam defines an optical train and generates a back-scattering light pattern; and iii) a photodetector configured to detect the back-scattering light pattern; and b) an electronics assembly comprising circuitry for a temperature control unit configured to control a temperature of a medium through which the optical train travels and a temperature of the microfluidic chip;

wherein said optical train and chip are thermally separated from said photodetector and said optical assembly is thermally separated from said electronics assembly.

12. The device of claim 11, wherein said temperatures are controlled by at least one heat pump.

13. The device of claim 12, wherein the heat pump is a Peltier device.

14. The device of claim 11, wherein the electronics assembly further comprises circuitry for an instrument control unit, wherein the instrument control unit communicates with at least one of the coherent light source and the photodetector.

15. The device of claim 11, wherein the sensing area has a volume of no more than 10 nl.

16. The device of claim 11, further comprising an optical enclosure that thermally separates the optical train from the photodetector, wherein the enclosure is configured to allow the back-scattering light pattern to reach the photodetector.

17. The device of claim 11, wherein the temperature of said medium through which the optical train travels is maintained within 500 m° C. of a second target temperature.

18. The device of claim 11, wherein the temperature of said chip is maintained within 20 m° C. of a first target temperature.

19. The device of claim 11 wherein the coherent light source is selected from a He/Ne laser, a VCSEL laser and a diode laser.

20. The device of claim 11 wherein the photodetector comprises a CCD or CMOS camera.

21. The device of claim 11, wherein the temperature of said medium through which the optical train travels is maintained within 100 m° C. of a second target temperature.

22. A method comprising:

operating an interferometric device that detects an interference pattern generated from a sensing area of a microfluidic chip by directing light from a coherent light source along an optical train through an enclosure comprising a medium toward said sensing area; and maintaining a temperature of the chip to within 20 m° C. of a first target temperature and maintaining a temperature of the medium within 500 m° C. of a second target temperature under conditions in which ambient temperature changes from 0.1° C. to 5° C. over 5 minutes.

23. The method of claim 22 wherein the temperature of the chip is maintained to within 5 m° C. while a sample is being examined.

24. The method of claim 22 wherein the coherent light source is selected from a He/Ne laser, a VCSEL laser and a diode laser.

25. The method of claim 22 comprising maintaining a temperature of the medium within 100 m° C. of a second target temperature.

26. A method of maintaining temperature within an interferometer comprising:

a) detecting temperature (1) at a sensing area of a microfluidic chip within the interferometer, (2) of a medium within an enclosure through which an optical train travels between a coherent light source and the sensing area and (3) of a ambient environment; and b) regulating activity of a first heat pump in thermal contact with the microfluidic chip and a second heat pump in thermal contact with the medium as a function of the measured temperatures.

27. The method of claim 26 wherein the coherent light source is selected from a He/Ne laser, a VCSEL laser and a diode laser.

28. The method of claim 26 wherein the heat pump in contact with the microfluidic chip comprises a Peltier.

29. The method of claim 26 wherein regulating comprises maintaining temperature at the sensing area to within 5 m° C. while a sample is being examined.

30. The method of claim 29 wherein the temperature of the medium is maintained within 100 m° C. of a second target temperature.

31. The method of claim 26 wherein the temperature of said sensing area is maintained within 20 m° C. of a first target temperature and the temperature of the medium is maintained within 500 m° C. of a second target temperature.

* * * * *